United States Patent [19]

Tuomanen et al.

[11] Patent Number: 5,817,617
[45] Date of Patent: Oct. 6, 1998

[54] SELECTIN AND PERTUSSIS TOXIN DERIVED PEPTIDES AND USES THEREOF

[75] Inventors: Elaine Tuomanen; H. Robert Masure, both of New York, N.Y.

[73] Assignee: The Rockefeller University, New York, N.Y.

[21] Appl. No.: 140,137

[22] PCT Filed: May 4, 1992

[86] PCT No.: PCT/US92/03701

§ 371 Date: May 27, 1994

§ 102(e) Date: May 27, 1994

Related U.S. Application Data

[63] Continuation-in-part of Ser. No. 695,532, May 3, 1991, abandoned.

[51] Int. Cl.$^6$ ........................ A61K 38/00; A61K 39/395; C07K 14/00; C07K 16/18

[52] U.S. Cl. .................................. 514/2; 514/8; 514/885; 530/300; 530/324; 530/327; 530/387.9; 530/388.2; 530/388.22; 530/388.4; 530/388.7; 530/388.73; 530/388.75; 424/139.1; 424/143.1; 424/144.1; 424/150.1; 424/153.1; 424/154.1; 424/173.1

[58] Field of Search .............................. 424/130.1, 134.1, 424/139.1, 140.1, 141.1, 143.1, 144.1, 152.1, 153.1, 154.1, 156.1, 172.1, 173.1, 174.1, 150.1; 514/2, 8, 885; 530/300, 350, 387.1, 387.9, 380.1, 388.22, 388.7, 388.73, 388.75, 388.85, 324, 327, 388.2, 388.4

[56] References Cited

U.S. PATENT DOCUMENTS 5,081,034  1/1992  Bevilacqua et al. .
5,216,131  6/1993  Lasky et al. ............................ 530/350

FOREIGN PATENT DOCUMENTS 0 030 496  11/1980  European Pat. Off. .
WO 90/05786  5/1990  WIPO .
WO 92/01718  2/1992  WIPO .
WO 92/19646  11/1992  WIPO .

OTHER PUBLICATIONS

Saukkonen et al.(1992), Proc. Natl. Acad. Sci. USA 89:118–122.
Nourshargh et al.(1990), J. Immunology 145:2633–2638.
Sato et al.(1987),Infection and Immunity 55:909–915.
Sato et al.(1990), Infection and Immunity 58:3369–3374.
Schmidt et al.(1989), Infection and Immunity 57:3828–3833.
Burnette et al.(1988), Biotechnology 6:699–706.
Nicosia et al.(1986), Proc. Natl. Acad. Sci. USA 83:4631–4635.
Johnston et al.(1989), Cell 56:1033–1044.
Brandley et al.(1990), Cell 63:861–863.
Geng et al.(1991), J. Biological Chemistry 266:22313–22318.
Relman et al.(1989), Proc. Natl. Acad. Sci. USA 86:2637–2641.
Relman et al.(1990), Cell 61:1375–1382.
Tuomanen et al.(1989), J. Exp. Med. 170:959–968.
Dermietzel et al.(1991), International Review of Cytology 127:57–109.
Springer et al.(1991), Nature 349:196–197.
Lobet et al.(1989), Infection and Immunity 57:3660–2662.
Saukkonen et al.(1990), Sixth Internat. Symp. Pertus., Bethesda,Sep.26–28,15:117–118.
Bowen et al.(1989), J. Cell Biology 109:421–427.
Osborn(1990), Cell 62:3–6.
Witvliet et al.(1989), Infection and Immunity 57:3324–3330.
Batley et al.(1989), Proc. Natl. Acad. Sci. USA 86:8353–8357.
Sandros et al.(1994), Glycoconjugate J. 11:501–506.
Sandros et al.(1994), Microbial Pathogenesis 16:213–220.
Rozdzinski et al.(1993),J. Exp. Med. 178:917–924.
Rozdzinski et al.(1993), J. Infections Diseases 168:1422–1428.
Harris et al.(1993), TIB.Tech. 11:42–44.
Kahan(1992), Curr. Opin. in Immuno. 4:553–560.
Edgington(1992), Biotechnology 10:383–389.
Sherman–Gold(1993), Genetic Engineering News Jul. 6–7, 14.
Ward et al.(1994), Therapeutic Immunology !:165–171.
Burnette et al.(1988) Science 242:72–4.
Cieplak et al. (1988) Proc.Natl. Acad. 85:4667–71.
Katuda et al. (1982) Proc. Natl. Acad. Sci. 79:3129–33.
Locht et al. (1986) Science 232:1258–64.
Relman et al. (1990) Cell 61:1375–82.
Tuomanen et al. (1985) J. Infect. Dis. 152:118–25.

*Primary Examiner*—Lila Feisee
*Assistant Examiner*—Phillip Gambel
*Attorney, Agent, or Firm*—Klauber & Jackson

[57]  ABSTRACT

Proteins, peptides, analogs thereof and antibodies thereto which will inhibit the adhesion of circulating molecules such as leukocytes to endothelia and epithelia.

10 Claims, 12 Drawing Sheets

|  | A | C | HI | I S | EEQ | EV | H |
|---|---|---|---|---|---|---|---|
| CaRD |  |  |  |  |  |  |  |
| ELAM | 19Asay | Cqqryt | HL | valqnk | EEi | eylns | ilsys |
| hLHRc | 19Arrf | Crdnytd | L | valqnk | EEi | eylek | tlpfs |
| S3 | 19Aygr | Cpngtra | Ltvaelrgna | Ei | qtylrqit | pgws |
| GMP140 | 19srky | Cqnrytd | L | valqnk | rEi | dylnkv | lpyys |
| S2 | 19pygd | Canktral | tvaelrgsgddl | qev | lrhvtrgws |

```
     19      25        30        35        40        45        50        55        60
s3           aygrcpngtral tvaelrgnaelqtylrqitpgwsiyglyglydgty
s2   pygrcanktral tvaelrgsgdlqeylrhvtrgwsifalydgty
```

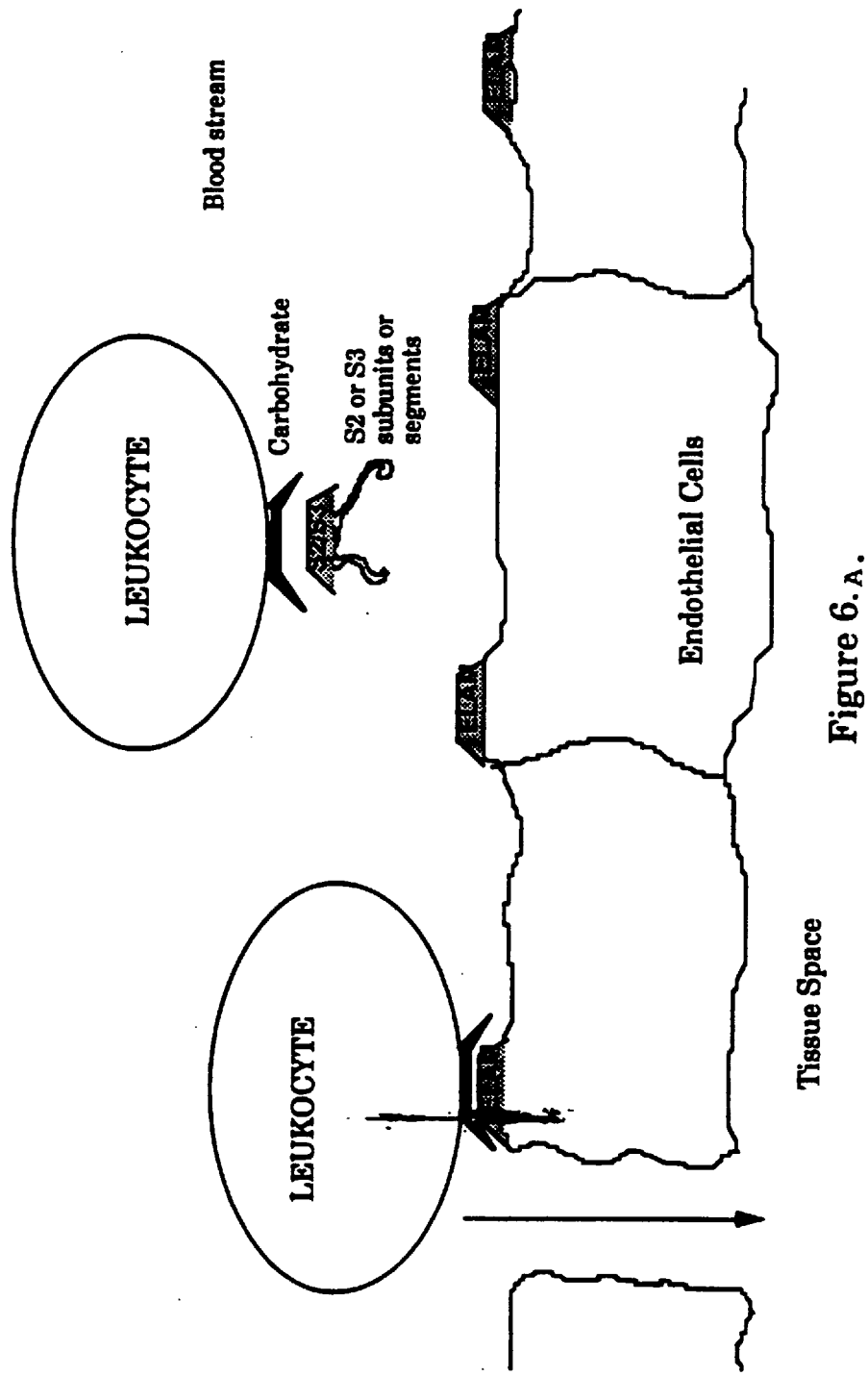
Figure 6.A.

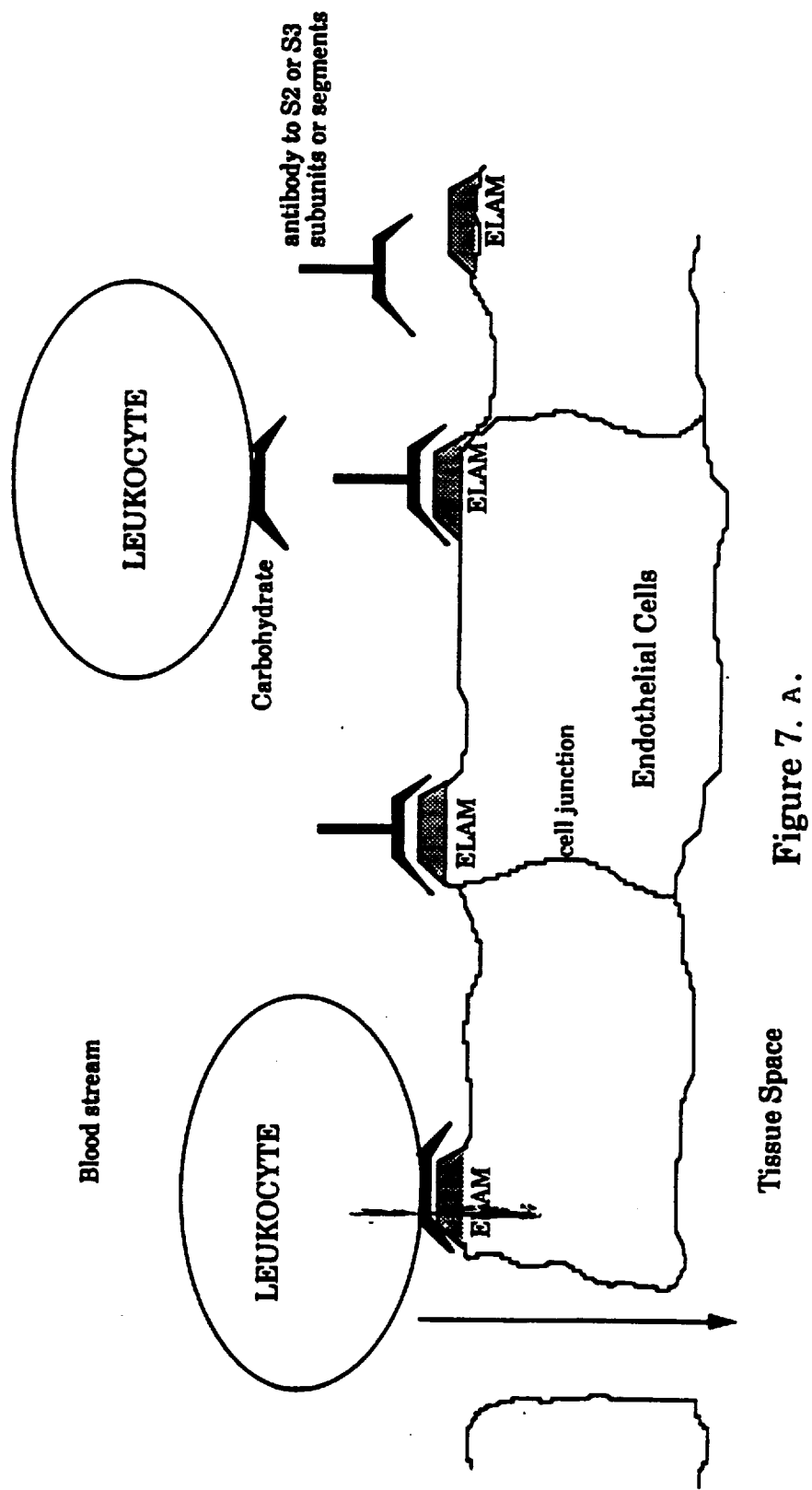

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide
       ( A ) DESCRIPTION: Xaa at position 8 may be any amino acid or
             not be present ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

Val  Ala  Ile  Gln  Asn  Lys  Glu  Xaa  Glu  Ile
   1                  5                        10

( 2 ) INFORMATION FOR SEQ ID NO:2:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide
       ( A ) DESCRIPTION: Xaa at position 7 may be any amino acid or
             not be present ( i i i ) HYPOTHETICAL: NO ( i v ) ANTI-SENSE: NO ( v ) FRAGMENT TYPE: internal ( x i ) SEQUENCE DESCRIPTION: SEQ ID NO:2:

Val  Ala  Ile  Gln  Asn  Lys  Xaa  Glu  Glu  Ile
   1                  5                        10

( 2 ) INFORMATION FOR SEQ ID NO:3:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide
       ( A ) DESCRIPTION: Xaa at position 6 may be any amino acid or
             not be present ( i i i ) HYPOTHETICAL: NO ( i v ) ANTI-SENSE: NO ( v ) FRAGMENT TYPE: internal ( x i ) SEQUENCE DESCRIPTION: SEQ ID NO:3:

Val  Ala  Ile  Gln  Asn  Xaa  Lys  Glu  Glu  Ile
   1                  5                        10

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide
        ( A ) DESCRIPTION: Xaa at position 5 may be any amino acid or not be present ( i i i ) HYPOTHETICAL: NO ( i v ) ANTI-SENSE: NO ( v ) FRAGMENT TYPE: internal ( x i ) SEQUENCE DESCRIPTION: SEQ ID NO:4:

Val Ala Ile Gln Xaa Asn Lys Glu Glu Ile
    1               5                     10

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide
        ( A ) DESCRIPTION: Xaa at position 4 may be any amino acid or not be present ( i i i ) HYPOTHETICAL: NO ( i v ) ANTI-SENSE: NO ( v ) FRAGMENT TYPE: internal ( x i ) SEQUENCE DESCRIPTION: SEQ ID NO:5:

Val Ala Ile Xaa Gln Asn Lys Glu Glu Ile
    1               5                     10

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide
        ( A ) DESCRIPTION: Xaa at position 3 may be any amino acid or not be present ( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

Val Ala Xaa Ile Gln Asn Lys Glu Glu Ile
    1               5                     10

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:7:

Val  Ala  Glu  Leu  Arg  Gly  Asn  Ala  Glu  Leu
        1                   5                        1 0

(2) INFORMATION FOR SEQ ID NO:8:

(i) SEQUENCE CHARACTERISTICS:
              (A) LENGTH: 9 amino acids
              (B) TYPE: amino acid
              (C) STRANDEDNESS: single
              (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:8:

Val  Ala  Glu  Leu  Arg  Gly  Asn  Glu  Leu
        1                   5

(2) INFORMATION FOR SEQ ID NO:9:

(i) SEQUENCE CHARACTERISTICS:
              (A) LENGTH: 9 amino acids
              (B) TYPE: amino acid
              (C) STRANDEDNESS: single
              (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:9:

Val  Ala  Glu  Leu  Arg  Gly  Ala  Glu  Leu
        1                   5

(2) INFORMATION FOR SEQ ID NO:10:

(i) SEQUENCE CHARACTERISTICS:
              (A) LENGTH: 9 amino acids
              (B) TYPE: amino acid
              (C) STRANDEDNESS: single
              (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:10:

Val  Ala  Glu  Leu  Arg  Asn  Ala  Glu  Leu
        1                   5

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:11:

Val  Ala  Glu  Leu  Gly  Asn  Ala  Glu  Leu
    1                     5

( 2 ) INFORMATION FOR SEQ ID NO:12:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:12:

Val  Ala  Glu  Arg  Gly  Asn  Ala  Glu  Leu
    1                     5

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:13:

Val  Ala  Leu  Arg  Gly  Asn  Ala  Glu  Leu
    1                     5

( 2 ) INFORMATION FOR SEQ ID NO:14:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide
        ( A ) DESCRIPTION: At position 9 only, Xaa is selected from the
                group consisting of Glu and Asp residues ( i i i ) HYPOTHETICAL: NO ( i v ) ANTI-SENSE: NO ( v ) FRAGMENT TYPE: internal ( x i ) SEQUENCE DESCRIPTION: SEQ ID NO:14:

```
Val Ala Xaa Xaa Xaa Xaa Xaa Xaa Xaa Xaa Xaa Xaa Xaa Leu
1               5                       10
```

( 2 ) INFORMATION FOR SEQ ID NO:15:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:15:

```
Val Ala Ile Gln Asn Lys Glu Glu Ile Glu Tyr Leu Asn Ser Ile Leu
1               5                       10                      15

Ser Tyr Ser
```

( 2 ) INFORMATION FOR SEQ ID NO:16:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:16:

```
Thr His Leu Val Ala Ile Gln Asn Lys Glu Glu Ile Glu Tyr Leu
1               5                       10                      15
```

( 2 ) INFORMATION FOR SEQ ID NO:17:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:17:

```
Thr Leu Val Ala Ile Gln Asn Glu Glu Ile Glu Tyr Leu
1               5                       10
```

( 2 ) INFORMATION FOR SEQ ID NO:18:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: NO (v) FRAGMENT TYPE: internal (x i) SEQUENCE DESCRIPTION: SEQ ID NO:18:

Val Ala Ile Gln Asn Lys Ala Glu Ile Glu Tyr Leu Glu Lys Thr Leu
1               5                   10                  15
Pro Phe Ser (2) INFORMATION FOR SEQ ID NO:19:

(i) SEQUENCE CHARACTERISTICS:
      (A) LENGTH: 15 amino acids
      (B) TYPE: amino acid
      (D) TOPOLOGY: linear (i i) MOLECULE TYPE: peptide (i i i) HYPOTHETICAL: NO (v) FRAGMENT TYPE: internal (x i) SEQUENCE DESCRIPTION: SEQ ID NO:19:

Thr Asp Leu Val Ala Ile Gln Asn Lys Ala Glu Ile Glu Tyr Leu
1               5                   10                  15

(2) INFORMATION FOR SEQ ID NO:20:

(i) SEQUENCE CHARACTERISTICS:
      (A) LENGTH: 22 amino acids
      (B) TYPE: amino acid
      (D) TOPOLOGY: linear (i i) MOLECULE TYPE: peptide (i i i) HYPOTHETICAL: NO (v) FRAGMENT TYPE: internal (x i) SEQUENCE DESCRIPTION: SEQ ID NO:20:

Val Ala Glu Leu Arg Gly Ser Asp Gly Leu Gln Glu Tyr Leu Arg His
1               5                   10                  15
Val Thr Arg Gly Trp Ser
                20

(2) INFORMATION FOR SEQ ID NO:21:

(i) SEQUENCE CHARACTERISTICS:
      (A) LENGTH: 17 amino acids
      (B) TYPE: amino acid
      (D) TOPOLOGY: linear (i i) MOLECULE TYPE: peptide (i i i) HYPOTHETICAL: NO (v) FRAGMENT TYPE: internal (x i) SEQUENCE DESCRIPTION: SEQ ID NO:21:

Gln Asn Lys Asn Glu Ile Asp Tyr Leu Asn Lys Val Leu Pro Tyr Tyr
1               5                   10                  15
Ser (2) INFORMATION FOR SEQ ID NO:22:

(i) SEQUENCE CHARACTERISTICS:
      (A) LENGTH: 18 amino acids
      (B) TYPE: amino acid
      (D) TOPOLOGY: linear (i i) MOLECULE TYPE: peptide (iii) HYPOTHETICAL: NO (v) FRAGMENT TYPE: internal (xi) SEQUENCE DESCRIPTION: SEQ ID NO:22:

Arg Ala Leu Thr Val Ala Glu Leu Arg Gly Ser Gly Asp Leu Gln Glu
1               5                   10                  15

Tyr Leu (2) INFORMATION FOR SEQ ID NO:23:

(i) SEQUENCE CHARACTERISTICS:
      (A) LENGTH: 16 amino acids
      (B) TYPE: amino acid
      (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:23:

Ala Leu Thr Val Ala Glu Leu Gly Ser Gly Asp Leu Gln Glu Tyr Leu
1               5                   10                  15

(2) INFORMATION FOR SEQ ID NO:24:

(i) SEQUENCE CHARACTERISTICS:
      (A) LENGTH: 22 amino acids
      (B) TYPE: amino acid
      (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:24:

Val Ala Glu Leu Arg Gly Asn Ala Glu Leu Gln Thr Tyr Leu Arg Gln
1               5                   10                  15

Ile Thr Pro Gly Trp Ser
                20

(2) INFORMATION FOR SEQ ID NO:25:

(i) SEQUENCE CHARACTERISTICS:
      (A) LENGTH: 18 amino acids
      (B) TYPE: amino acid
      (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:25:

Arg Ala Leu Thr Val Ala Glu Leu Arg Gly Asn Ala Glu Leu Gln Thr
1               5                   10                  15

Tyr Leu (2) INFORMATION FOR SEQ ID NO:26:

(i) SEQUENCE CHARACTERISTICS:
      (A) LENGTH: 16 amino acids
      (B) TYPE: amino acid (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:26:

Ala Leu Thr Val Ala Glu Leu Gly Asn Ala Glu Leu Gln Thr Tyr Leu
1               5                   10                  15

(2) INFORMATION FOR SEQ ID NO:27:

(i) SEQUENCE CHARACTERISTICS:
(A) LENGTH: 32 amino acids
(B) TYPE: amino acid
(D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:27:

Thr Val Ala Glu Leu Arg Gln Asn Glu Leu Gln Thr Tyr Leu Arg Gln
1               5                   10                  15

Ile Thr Pro Gly Trp Ser Ile Thr Gly Leu Tyr Asp Thr Val Ala Ile
                20                  25                  30

(2) INFORMATION FOR SEQ ID NO:28:

(i) SEQUENCE CHARACTERISTICS:
(A) LENGTH: 24 amino acids
(B) TYPE: amino acid
(D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:28:

Thr Val Ala Glu Leu Arg Gly Ser Gly Asp Leu Gly Glu Tyr Leu Arg
1               5                   10                  15

His Val Thr Arg Gly Trp Ser Ile
                20

(2) INFORMATION FOR SEQ ID NO:29:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO:29:

Lys Glu Glu Ile Glu Tyr Leu Asn Ser Ile Leu Ser Tyr Ser
1               5                   10

(2) INFORMATION FOR SEQ ID NO:30:

(i) SEQUENCE CHARACTERISTICS:
(A) LENGTH: 14 amino acids
(B) TYPE: amino acid
(D) TOPOLOGY: linear ( i i ) MOLECULE TYPE: peptide ( x i ) SEQUENCE DESCRIPTION: SEQ ID NO:30:

Thr Leu Val Ala Ile Gln Asn Lys Glu Glu Ile Glu Tyr Leu
1               5                   10

( 2 ) INFORMATION FOR SEQ ID NO:31:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:

Val Ala Ile Gln Asn Lys Ala Glu Ile Glu Tyr Leu Glu Lys Thr Leu
1               5                   10                  15

Pro Phe Ser ( 2 ) INFORMATION FOR SEQ ID NO:32:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

Ala Glu Leu Gln Thr Tyr Leu Arg Gln Ile Thr Pro Gly Trp Ser
1               5                   10                  15

( 2 ) INFORMATION FOR SEQ ID NO:33:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:33:

Val Ala Ile Gln Asn Lys Asn Glu Ile Asp Tyr Leu Asn Lys Val Leu
1               5                   10                  15

Pro Tyr Tyr Ser
                20

( 2 ) INFORMATION FOR SEQ ID NO:34:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

Val Ala Glu Leu Arg Gly Ser Gly Asp Leu Gln Glu Tyr Leu Arg His
1               5                   10                  15

Val Thr Arg Gly Trp Ser
                20

( 2 ) INFORMATION FOR SEQ ID NO:35:

( i ) SEQUENCE CHARACTERISTICS:
        ( A ) LENGTH: 15 amino acids (B) TYPE: amino acid
(D) TOPOLOGY: linear (i i) MOLECULE TYPE: peptide (x i) SEQUENCE DESCRIPTION: SEQ ID NO:35:

Gly Asp Leu Gln Glu Tyr Leu Arg His Val Thr Arg Gly Trp Ser
1               5                   10                  15

(2) INFORMATION FOR SEQ ID NO:36:

(i) SEQUENCE CHARACTERISTICS:
(A) LENGTH: 16 amino acids
(B) TYPE: amino acid
(D) TOPOLOGY: linear (i i) MOLECULE TYPE: peptide (x i) SEQUENCE DESCRIPTION: SEQ ID NO:36:

Ala Leu Thr Val Ala Glu Leu Gly Ser Gly Asp Leu Gln Glu Tyr Leu
1               5                   10                  15

(2) INFORMATION FOR SEQ ID NO:37:

(i) SEQUENCE CHARACTERISTICS:
(A) LENGTH: 24 amino acids
(B) TYPE: amino acid
(D) TOPOLOGY: linear (i i) MOLECULE TYPE: peptide (x i) SEQUENCE DESCRIPTION: SEQ ID NO:37:

Thr Arg Ala Leu Thr Val Ala Glu Leu Arg Gly Asn Ala Glu Leu Gln
1               5                   10                  15
Thr Tyr Leu Arg Gln Ile Thr Pro
                20

(2) INFORMATION FOR SEQ ID NO:38:

(i) SEQUENCE CHARACTERISTICS:
(A) LENGTH: 20 amino acids
(B) TYPE: amino acid
(D) TOPOLOGY: linear (i i) MOLECULE TYPE: peptide (x i) SEQUENCE DESCRIPTION: SEQ ID NO:38:

Thr Arg Ala Leu Thr Arg Gly Asn Ala Glu Leu Gln Thr Tyr Leu Arg
1               5                   10                  15
Gln Ile Thr Pro
                20

(2) INFORMATION FOR SEQ ID NO:39:

(i) SEQUENCE CHARACTERISTICS:
(A) LENGTH: 16 amino acids
(B) TYPE: amino acid
(D) TOPOLOGY: linear (i i) MOLECULE TYPE: peptide (x i) SEQUENCE DESCRIPTION: SEQ ID NO:39:

Thr Arg Ala Leu Thr Val Ala Glu Leu Arg Gly Asn Ala Ile Thr Pro
1               5                   10                  15

(2) INFORMATION FOR SEQ ID NO:40:

(i) SEQUENCE CHARACTERISTICS:

( A ) LENGTH: 23 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:40:

Val Ala Ile Val Ala Ile Gln Asn Lys Asn Glu Ile Asp Tyr Leu Asn
1               5                   1 0                      1 5

Lys Val Leu Pro Tyr Tyr Ser
                2 0

( 2 ) INFORMATION FOR SEQ ID NO:41:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:41:

Thr Val Ala Glu Leu Arg Gln Asn Glu Leu Gln Thr Tyr Leu Arg Gln
1               5                   1 0                      1 5

Ile Thr Pro Gly Trp Ser Ile Tyr Gly Leu Tyr Asp Gly Thr
                2 0                  2 5                 3 0

( 2 ) INFORMATION FOR SEQ ID NO:42:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide
        ( A ) DESCRIPTION: CaRD peptide seqence ( x i ) SEQUENCE DESCRIPTION: SEQ ID NO:42:

Ala Cys His Leu Ile Ser Glu Glu Gln Phe Val His
1               5                   1 0

( 2 ) INFORMATION FOR SEQ ID NO:43:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide
        ( A ) DESCRIPTION: ELAM peptide seqence ( x i ) SEQUENCE DESCRIPTION: SEQ ID NO:43:

Ala Ser Ala Tyr Cys Gln Gln Arg Tyr Thr His Leu Val Ala Ile Gln
1               5                   1 0                      1 5

Asn Lys Glu Glu Ile Glu Tyr Leu Asn Ser Ile Leu Ser Tyr Ser
                2 0                  2 5                 3 0

( 2 ) INFORMATION FOR SEQ ID NO:44:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide
        ( A ) DESCRIPTION: hLHRc peptide seqence ( x i ) SEQUENCE DESCRIPTION: SEQ ID NO:44:

Ala Arg Arg Phe Cys Arg Asp Asn Tyr Thr Asp Leu Val Ala Ile Gln
1               5                   10                  15

Asn Lys Ala Glu Ile Glu Tyr Leu Glu Lys Thr Leu Pro Phe Ser
                20              25                  30

( 2 ) INFORMATION FOR SEQ ID NO:45:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide
        ( A ) DESCRIPTION: S3 peptide seqence ( x i ) SEQUENCE DESCRIPTION: SEQ ID NO:45:

Ala Tyr Gly Arg Cys Pro Asn Gly Thr Arg Ala Leu Thr Val Ala Glu
1               5                   10                  15

Leu Arg Gly Asn Ala Glu Leu Gln Thr Tyr Leu Arg Gln Ile Thr Pro
                20              25                  30

Gly Trp Ser
        35

( 2 ) INFORMATION FOR SEQ ID NO:46:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide
        ( A ) DESCRIPTION: GMP140 peptide seqence ( x i ) SEQUENCE DESCRIPTION: SEQ ID NO:46:

Ser Arg Lys Tyr Cys Gln Asn Arg Tyr Thr Asp Leu Val Ala Ile Gln
1               5                   10                  15

Asn Lys Asn Glu Ile Asp Tyr Leu Asn Lys Val Leu Pro Tyr Tyr Ser
                20              25                  30

( 2 ) INFORMATION FOR SEQ ID NO:47:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide
        ( A ) DESCRIPTION: S2 peptide seqence ( x i ) SEQUENCE DESCRIPTION: SEQ ID NO:47:

Pro Tyr Gly Arg Cys Ala Asn Lys Thr Arg Ala Leu Thr Val Ala Glu
1               5                   10                  15

Leu Arg Gly Ser Gly Asp Leu Gln Glu Tyr Leu Arg His Val Thr Arg
                20              25                  30

Gly Trp Ser
        35

( 2 ) INFORMATION FOR SEQ ID NO:48:

( i ) SEQUENCE CHARACTERISTICS:
        ( A ) LENGTH: 44 amino acids
        ( B ) TYPE: amino acid
        ( D ) TOPOLOGY: linear ( i i ) MOLECULE TYPE: peptide
        ( A ) DESCRIPTION: S3 peptide seqence -continued (xi) SEQUENCE DESCRIPTION: SEQ ID NO:48:

```
Ala Tyr Gly Arg Cys Pro Asn Gly Thr Arg Ala Leu Thr Val Ala Glu
1               5                   10                  15

Leu Arg Gly Asn Ala Glu Leu Gln Thr Tyr Leu Arg Gln Ile Thr Pro
            20                  25                  30

Gly Trp Ser Ile Tyr Gly Leu Tyr Asp Gly Thr Tyr
        35                  40
```

(2) INFORMATION FOR SEQ ID NO:49:

(i) SEQUENCE CHARACTERISTICS:
   (A) LENGTH: 44 amino acids
   (B) TYPE: amino acid
   (D) TOPOLOGY: linear (ii) MOLECULE TYPE: peptide
   (A) DESCRIPTION: S2 peptide seqence (xi) SEQUENCE DESCRIPTION: SEQ ID NO:49:

```
Pro Tyr Gly Arg Cys Ala Asn Lys Thr Arg Ala Leu Thr Val Ala Glu
1               5                   10                  15

Leu Arg Gly Ser Gly Asp Leu Gln Glu Tyr Leu Arg His Val Thr Arg
            20                  25                  30

Gly Trp Ser Ile Phe Ala Leu Tyr Asp Gly Thr Tyr
        35                  40
```

SELECTIN AND PERTUSSIS TOXIN DERIVED PEPTIDES AND USES THEREOF

RELATED APPLICATION

This application is a continuation in part of application Ser. No. 07/695,532 filed May 3, 1991, now abandoned the disclosure of which is incorporated herein by reference.

This invention was made with government support under Grant Number AI23459 awarded by the National Institutes of Health. The Government has certain rights in the invention.

BACKGROUND OF THE INVENTION

The seminal discovery of this invention is that there is structural and functional homology between two proteins from *Bordetella pertussis* (BP) and a family of eukaryotic proteins called selectins. This homology gives rise to two of the more important aspects of the invention. First, these BP proteins, called pertussis toxin (PT) subunits S2 and S3, and segments of these products can act as analogs of the selectins. Secondly, antibodies to S2 and S3, or segments thereof, can block the functions of selectins.

BP is the Gram-negative prokaryotic bacillus responsible for pertussis or whooping cough, [Bordet, J. & Gengou, O. *Ann. Inst. Pasteur* 20, 731–741 (1906)]. It has been extensively studied and its mode of action is quite well understood. Several vaccines have been proposed based upon the complete organism or purified proteins derived from it. None are completely satisfactory.

During the course of a whooping cough infection, BP attaches specifically to the ciliated epithelium and produces systemic disease by elaborating several toxins, one of which is PT. PT is a major virulence determinant which induces metabolic changes such as hypoglycemia and increased vascular permeability.

PT is a hexameric protein with an A-B (Active-Binding) architecture. The A promoter of PT is composed of a single subunit carrying the catalytically active ADP-ribosylating site. The B oligomer contains the cellular recognition domains and is a complex pentamer containing subunits S2, S3, S4 and S5 in the molar ratio 1:1:2:1 and with molecular weights 21,925; 21,873, 12,025 and 11,013 Da, respectively, [Katuda, T. & Ui, M. *Proc. Natl. Acad. Sci.* 79, 3129–3133 (1982)]. S2 and S3 exhibit about 80% homology at the level of nucleotide sequence of the genes. In addition to binding the toxin to its target eukaryotic cells, these subunits also mediate the adhesion of BP to ciliated cells and leukocytes because of their ability to bind to eukaryotic carbohydrates.

The genes that code for S2 and S3 have been cloned and sequenced and the expected recombinant proteins expressed, [Biotechnology 6:699, (1988); Locht and Keith, Science, 232:1258, (1986); Nicosia et al, Proc Natl Acad Sci 83:4631, (1986)]. Recombinant proteins can be purified from inclusion bodies isolated from expression systems, for instance in *E. coli*. Subcloning and mutation of the subunits by the technique has been accomplished to produce analogs and segments of S2 and S3. Burnette, N., et al (1988) Biotechnology 6,699–706; Burnette, N., et al J. (1988 Science 242,72–74; Cieplak, W., Burnette, et al, J. (1988) Proc. Natl. Acad. Sci. U.S. A. 85,4667–4671.

Selectins (or LEC-CAMs) are a family of cell adhesion molecules that have been implicated in the interaction of leukocytes with platelets or vascular endothelium. Adhesion is a prerequisite for diapedesis of leukocytes through endothelium, and is also necessary for leukocytes homing, a process in which leukocytes exit the blood stream at specific high endothelial venules in lymphoid tissues. [Brandley et al., Cell, 63:861–3, (1990)]. Selectins recognize carbohydrates for example carbohydrate receptors on leukocytes. Members of the selectin family include ELAM (Endothelial Leukocyte Adhesion Molecule), hLHR (human Lymphocyte Homing Receptor), and GmP 140 (Granual Membrane Protein). ELAM is located on the endothelial cell and is synthesized by the cells in response to inflammatory agents. Interference with its functions prevents leukocyte adhesion to endothelium. hLHR is located on lymphocytes. Interference with its function prevents the normal homing of these cells to lymphoid tissue (e.g. lymph note, Peyer's patches, bronchial lymphoid tissue). GMP 140 is expressed by endothelial cells and platelets and, in a manner not as yet understood, promotes leukocyte adhesion to endothelium and platelets.

SUMMARY OF THE INVENTION

This invention is based on the discovery that there is structural and functional homology between PT, more specifically subunits S2 and S3 of PT, and the selectins ELAM, GMP 140, and hLHR. This is the first recognition of such homology between proteins from prokaryotic and eukaryotic cells. Thus PT, the B oligomer of PT its subunits S2 and S3 and segments thereof can act as analogs of these selecting. Of equal significance is the fact that antibodies to these proteins and segments can block the functions of selectins.

There are a number of significant consequences of this important discovery. These are:

1. PT, the B-oligomer of PT, S2 or S3 and peptides derived from these proteins will mimic selectins and bind to the carbohydrate receptors on eukaryotic cells and thereby prevent the adherence of such circulating cells to the endothelial cells and inhibit the inflammatory, metastatic or coagulation processes. Such peptides can also function as carriers to direct selected therapeutic agents to cells bearing selectin-specific carbohydrate receptors, such as leukocytes, platelets, or high endothelial venules.

2. Antibodies to PT, the B oligomer of PT, S2 or S3 or to peptides derived from these proteins may be used to block selectins and inhibit their participation in processes such as lymphocyte homing, inflammation metastasis, coagulation etc. By binding to carbohydrates on endothelia and epithelia, these antibodies also can serve to deliver therapeutic agents to these sites.

3. Antibodies to PT, the B oligomer of PT, S2 or S3 or peptides derived from these proteins will prevent binding of BP to eukaryotic cells such as ciliated cells and macrophages. This inhibition interferes with the persistence of BP infection of the host. These proteins themselves and peptides derived from them will function as vaccines to protect against BP infections because they will generate antibodies which will inhibit adherence of BP to cilia and leukocytes.

Those skilled in the art will recognize that there are at least two fundamental procedures for taking advantage of the discovery upon which this invention is based. One involves the utilization of antibodies to block bacterial adherence or the described selectin-dependent adherence of eukaryotic cells. These are exemplified by procedures 2 and 3. Procedure 1, on the other hand prevents such adhesion by blocking the carbohydrate receptors on leukocytes utilizing the described peptides.

This invention is directed to PT, its B-oligomer, S2, S3, segments of these proteins, peptides derived from any of them and analogs of these products as well as antibodies to these products and analogs which are capable of inhibiting adhesion between leukocytes and endothelia. It is also directed to pharmaceutical compositions containing the products and to therapeutic use of such products to inhibit or prevent such adhesion and to other uses which flow from these basic properties. The invention relates also to genes which may be used in accordance with known techniques to produce proteins and protein segments employed in the invention.

The understanding of this invention will be facilitated if certain of the terms used in the description thereof are defined.

The term "peptide" is used in the most generic sense to include those peptides which contain only a few amino acid residues, e.g. 12 or more and also to include polypeptides containing 35 or more amino acids. The term is, perhaps, best understood in terms of the function the peptides perform. These functions include inhibition of adhesion between a selectin and a carbohydrate receptor. A peptide or analog may do so because its binds to and blocks a carbohydrate receptor on a eukaryotic cell or because antibodies to the peptide bind to a bacteria and prevent infection.

The term "antibodies" encompasses antibodies both polyclonal and monoclonal which bind to endothelia or epithelia. The preferred antibody is a monoclonal antibody. The term antibody is also intended to encompass mixtures of more than one antibody (e.g., a cocktail of different types of monoclonal antibodies). The term antibody is further intended to encompass whole antibodies, single chain antibodies, chimeric antibodies comprising portions from more than one species, chimeric proteins comprising a functional portion of an antibody coupled by covalent or recombinant techniques to an intact protein or functional portion thereof that is not of antibody origin (i.e. a chimeric antibody-protein), bifunctional antibodies, biologically functional fragments of the aforementioned, etc. Biologically functional antibody fragments which can be used are those fragments sufficient for binding of the antibody fragment to FHA or the x-molecule.

The chimeric antibodies can comprise portions derived from two different species (e.g., human constant region and murine binding region). The portions derived from two different species can be joined together chemically by conventional techniques or can be prepared as a single contiguous protein using genetic engineering techniques. DNA encoding the proteins of both portions of the chimeric antibody can be expressed as a continguous protein.

The term "carbohydrate recognition domain" (CRD) refers to a region of a molecule which is responsible for binding the molecule to a carbohydrate on a eukaryotic cell. The molecule may be a protein such as a selectin, PT, the B-oligomer, S2 or S3. It may be a lower molecular weight segment of such proteins. It may be a polypeptide or even a relatively low molecular weight peptide provided only that it functions as a selectin by binding to a carbohydrate.

The invention provides protein, peptides and analogs thereof which as their principal property are capable of preventing or inhibiting adhesion between leukocytes and endothelia in mammals, including domestic animals and humans. The invention also provides antibodies to such proteins, peptides and analogs.

The presently preferred products of this invention are peptides and their analogs, especially S2 and S3 like peptides and analogs. These are preferred because they are relatively small molecules which can be readily prepared in pure form by chemical synthesis. It will be apparent as the description of the invention proceeds that the invention is not limited to S2 and S3 peptides, but these presently appear to be preferred. S2 or S3 like peptides, sometimes referred to hereinafter as S-subunit peptides or S-subunit segment peptides may be identical or substantially similar to a region on an S-subunit or subunit segment. They will be useful in this invention so long as they are capable of reducing or inhibiting adhesion between epithelia or endothelia and circulating cells such as leukocytes, or of raising antibodies having this properties. A peptide may be considered as substantially similar to an S-subunit of S-subunit segment if there is homology of at least 50%, preferably 70% between the peptide and the region. It will be clear from this definition that peptides of this invention may contain amino acid additions, deletions and/or substitutions compared to the amino acid sequence of an S-subunit. The peptides contemplated herein may be chemically synthesized such as by solid phase peptide synthesis or they may be prepared by subjecting the selected substrate to hydrolysis or other chemically disruptive processes whereby fragments of the molecule are produced. Alternatively, the peptides could be made in vitro or in vivo using recombinant DNA technology. In this case, the peptides may need to be synthesized in combination with other proteins and then subsequently isolated by chemical cleavage or the peptides may be synthesized in multiple repeat units. Furthermore, multiple antigen peptides could also be prepared according to the method of Tam et al, J. Am. Chem. Soc. 105 6442–6445 (1988). The selection of a method of producing the subject peptides will depend from factors such as the required type, quantity and purity of the peptides as well as ease of production and convenience.

The use of these peptides in vivo may first require their chemical modification since the peptides themselves may not have a sufficiently long serum and/or tissue half-life. Such chemically modified peptides are referred to herein as analogs. the term analogs extends to any functional chemical equivalent of a peptide characterized by its increased stability and/or efficacy in vivo or in vitro in respect of the practice of the invention. The term "analog" is also used herein to extend to any amino acid derivative of the peptides as described herein.

Analogs of the peptides contemplated herein include, but are not limited to, modifications to side chains, incorporation of unnatural amino acids and/or their derivatives during peptide synthesis and the use of crosslinkers and other methods which impose conformational constraint on the peptides or their analogs.

Examples of side chain modifications contemplated by the present invention include modifications of amino groups such as by reductive alkylation by reaction with an aldehyde followed by reduction with $NaBH_4$; amidination which methylacetimidate; acylation with acetic anhydride; carbamoylation of amino groups with cyanate; trinitrobenzylation of amino groups with 2, 4, 6, trinitrobenzene sulfphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3-butanedione, phenylglyoxal and glyoxal.

The carboxyl group may be modified by carbodiimide activation via O=acylisourea formation followed by subsequent derivatisation, for example, to a corresponding amide.

Sulfhydryl groups may be modified by methods such as carboxymethylation with iodoacetic acid or iodoacetamide;

performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodiacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid-, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides could be conformationally constrained by, for example, incorporation of C and N α-methylamino acids, introduction of double bonds between C and C atoms of amino acids and the formation of cyclic peptides or analogs by introducing covalent bonds such as forming an amide bond between the N and C termini, between two side chains or between a side chain and the N or C terminus.

The peptides of the invention or their analogs may be single length or in tandem or multiple repeats. A single type of peptide or analog may form the repeats or the repeats may be composed of different molecules including suitable carrier molecules.

The present invention, therefore, extends to peptides or polypeptides and amino acid and/or chemical analogs thereof corresponding to regions of S-subunits and S-subunit segments capable of, or responsible for, binding, associating or otherwise, interacting with leukocytes or parts thereof and thereby inhibit or reduce adhesion of circulating cells such as leukocytes to endothelia or epithelia.

The antibodies useful in the practice of this invention can be raised utilizing whole or native protein, and this will be the procedure usually employed to produce polyclonal antibodies. They can also be raised to fragments of PT, the B-oligomer, S2 or S3 produced by chemical or enzymatic cleavage of the native protein or peptides therefrom. They can be produced, and this is the preferred method, by raising monoclonal antibodies to purified native PT proteins or the expression products from segments of the appropriate genes produced according to known methods such as that of Burnette et al *Biotechnology*, supra. The expression products are polypeptides containing a sufficient number of amino acid residues to elicit an antibody response alone or when attached to other antigenic determinants. The antibodies can be produced in accordance with well known procedures for the production of monoclonal antibodies and derivatives thereof. These monoclonal antibodies are the preferred antibodies for the practice of this invention.

The presently preferred monoclonal antibodies are prepared by the procedure of Sato et al [*Infec. Immun.* 55:909 (1987)], the disclosure of which is incorporated herein. They include three anti-S2 antibodies 2H3, 3A12 and 9G8; the anti-S3 antibodies 7E10, 7G11, 6F8, 2E12 and 4G5; as well as G9A, 10BS, 11E6, 3F6 and 10C9 which are anti-S2 and anti-S3 antibodies. These antibodies are useful in this invention because they are raised against S2 and S3 proteins which are homologous with selectins as described herein. Antibodies to S1, S4 and S5 subunits are not useful because they are raised against proteins which are not homologous to selectins.

BRIEF DESCRIPTION OF THE FIGURES

FIGS. 1 SEQ ID NOS:42–47 and 2 SEQ ID NOS:48–49 illustrate the amino acid arrangement in the carbohydrate recognition segments of certain of the molecules of interest in connection with this invention.

FIGS. 3 to 8 are sketches or graphs which will be useful to explain the invention.

DISCUSSION OF THE DRAWINGS

It will be helpful at this point to discuss some of the information which can be gained from the figures and the studies which were conducted to obtain the information.

FIG. 1 SEQ ID NOS:42–47 illustrates the high degree of homology between segments of S2 and S3 and members of the selectin group. The figure shows segments of the molecules of interest numbered in the conventional manner from the amino terminus utilizing the conventional letter symbols for the amino acids.

Based on amino acid sequence similarity, a large number of eukaryotic proteins which recognize carbohydrates have been grouped together into a family; the C-type carbohydrate recognition domain (CRD) family. The selectins are a subgroup of this family. PT and its subcomponents, particularly S2 and S3 are the first prokaryotic products found to follow the C-type CRD motif.

The high degree of homology amongst the various molecules containing the C-type CRD will be apparent from the outlined sections of FIG. 1 SEQ ID NOS:42–47. It will also be apparent that the highest degree of homology between the selectin family and, S2 and S3 segments shown in the figure is from about-position 32 to 53 of the subunits. This relatively conserved region is a principal contributor to carbohydrate receptor recognition for S2 and S3 and is, therefore, important for carbohydrate recognition by selectins and other C-type CRD's. It is also a preferred source of peptides for use in this invention in reactions involving carbohydrate recognition by these molecules or for eliciting useful antibodies.

The variability in the S2 and S3 segments shown in FIG. 1 SEQ ID NOS:42–47 is, quite clearly responsible for the variation in carbohydrate binding properties of PT, S2 and S3 which have been observed. PT, for example when tested for binding activity binds to lactosylceramide, glucosylceramide, sulfatides and gangliosides. S2 and S3 both bind to glucosylceramide and sulfatides, but only S2 binds to lactosylaceramide and only S3 binds to gangliosides.

The ability of a protein such as S2 or S3 to recognize and bind to a carbohydrate is a function of factors in addition to the sequence of amino acid residues. Thus, although two proteins may contain segments of amino acid residues identically arranged, one may recognize a specific carbohydrate, and the other may not have the ability. There are many reasons for this seeming anomaly. They are concerned with the structure of the proteins, e.g. whether the folding arrangement of the protein is such that a particular amino acid segment is on the surface of the protein or in the interior, or whether a particular functional group on a specific amino acid, e.g. the hydroxyl group of tyrosine is directed outwardly or inwardly.

In accordance with this invention, it has been discovered that the CRD of S2 involves amino acid segment 31 to 54 and of S3 amino acid segment 31 to 61.

This is has been established by a series of mutations, the most important of which are termed "exchange" mutations and which will be best understood by consideration of FIGS. 2 and 3.

FIG. 2 SEQ ID NOS:48–49 shows the amino acid sequences of the portions of the S2 and S3 subunit segments which are of interest for an understanding of this invention. More specifically, the boxes emphasize positions 31 to 54 on S2 and 31 to 61 on S3.

FIG. 3 shows the specific carbohydrates recognized by PT, S2, S3, and the protein S2/S3 in which the amino acid segment 31 to 54 of S2 has been replaced by the procedure of Burnette et al, supra with amino acid segment 31 to 61 from S3. The last column shows the recognition profile of S3/S2 in which amino acid segment 31 to 61 of S3 has been replaced with amino acid segment 31 to 54 from S2. The peptides S2/S3 and S3/S2 are novel therapeutic agents and are specifically included within the scope of this invention, as are the genes which express them.

In FIG. 3, the dark bars represent the positions of glycolipids after separation by thin layer chromatography in accordance with the method of Tuomanen et al, *J. Exp Med* 168:267, 1988.

S2/S3 and S3/S2 used in this study were produced by known methods from plasmids carrying the appropriate genes and transformed into *E. coli*. The plasmids carrying the genes are produced by known techniques from readily available restriction enzymes and plasmids. The procedures are fully described in Burnette et al, supra.

It will be seen that PT contains segments which recognize lactosylaceramide, and gangliosides. S2, S3, S2/S3 and S3/S2 have different carbohydrate recognition profiles. The most significant difference is that when segment 31 to 61 of S3 is used to replace segment 31 to 54 of S2, the resulting peptide then has recognition properties similar to S3. When a comparable exchange of an S2 segment is affected into S3, that subunit then assume the identical recognition portrait of S2. The 31 to 61 segment of S3 and the 31 to 54 segment of S2, as are the genes segments that express them, are novel and are within the ambit of the invention.

This test establishes unequivocally that the region of the CRD of S3 which determines carbohydrate specificity involves segment 31 to 54, and the CRD of S3 involves segment 31 to 61. It establishes also, that antibodies to those segments or smaller segments selected from them as well as additions, deletions and substitutions therein will be amongst the products useful in the practice of this invention. The segments themselves, and derivatives thereof, containing a CRD will, of course, be useful as antigens in vaccines for raising antibodies which bind selectins and also as inhibitors of selectins. Alternatively, derivatives of S2 or S3 with altered CRD's producing antibodies not cross reactive with selectins will be useful prophylactically as vaccines for whooping cough. The genes which produce all of these products are novel and within the scope of the invention. They are produced by standard procedures well within the skill of the art.

Similar results were obtained in vivo when S2, S3, S2/S3, and S3/S2 were tested for the ability to mediate adhesion of a particle (BPTOX6 or BP101/TOX6) to cilia or macrophages. It was found that by exchange mutations S2 could be made to act like S3, and S3 to act like S2 as shown in Table 1 below.

The ability of PT or the individual subunits to act as adhesins for PT-deficient bacteria to eukaryotic cells was assessed as described by Tuomanen et al (1985). *Infect. Dis.* 153, 118–125 and Relman et al (199) Cell 61, 1375–1382. It has been shown that a *B. pertussis* mutant deficient in PT production (BPTOX6) does not adhere to cilia and that a double mutant altered in both PT and filamentous hemagglutinin production (PB101/TOX6) fails to adhere to macrophages; in both cases, adherence can be reconstituted by addition of exogenous PT. For the test reported in Table 1 PT or its individual subunits (50 ug/ml) were incubated for 30 minutes with strain BPTOX6 for ciliated cell assays or BP101/TOX6 for macrophage assays in order to coat the bacteria with adhesin. $10^7$ bacteria were then incubated for 3 hours with $10^5$ ciliated cells or alveolar macrophages harvested from healthy rabbits (2,4). Adherence was detected by staining of the bacteria with a 1:40 dilution of fluorescein conjugated anti-Bordetella antibody (Difco, Detroit, Mich.). Values are expressed as the mean ±standard deviation of the number of bacteria per eukaryotic cell, 25 cells/test, and each test repeated in triplicate. The procedure is described in more detail in Saukkonen et al Proc. Natl. Acad. Sci. 89,118–122 (1991).

TABLE 1

Reconstitution of adherence of mutants of *B. pertussis* by exagenous PT and subunits S2 or S3.

| PT component added | Number of bacteria/target cell* | |
|---|---|---|
| | Macrophage | Ciliated Cell |
| none | <1 | <0.1 |
| PT | 21 ± 2.3 | 6.7 ± 0.8 |
| S2 | 1 | 7.3 ± 1.4 |
| S3 | 17 ± 1.3 | <0.1 |
| S2/2S3 | 27 ± 3.1 | <0.1 |
| S3/2S2 | 1 | 3.8 ± 0.3 |

These tests illustrate two features of the S2 and S3 CRDs (1) they are functional in assays where carbohydrates are presented on natural cells and (2) they can be used to target a particle or molecule to a specific type of cell i.e. S2 targets ciliated cells and S3 targets macrophages.

S2 and S3 segments useful in the practice in this invention will normally contain at least twelve and up to about 35 amino acid segments in order to be capable of raising antibodies either as individual antigens or as antigens attached to a carrier. Preferably, this will contain from 12 to 20 residues since these are easier to prepare.

In the balance of this disclosure, reference will be made principally to S2 and S3 since these and their various segments and modifications such as S2/S3 and S3/S2 are preferred species for the practice of this invention. For convenience, they will sometimes be referred to as S-subunits. Additionally, the invention will be principally discussed with reference to ELAM as a representative selectin, although it will be recognized that the invention is not limited to this selectin. Leukocyte adhesion will also be emphasized as an example of circulating eukaryotic cells such as tumor cells and platelets.

It will be understood, of course that PT and the B oligomer of PT will include in their protein structure the cell recognition sites of both S2 and S3 and the segments of the S2 and S3 shown in FIGS. 1 and 2.

DETAILED DESCRIPTION OF THE INVENTION

There are a number of novel and inventive products and processes which have been derived based on this invention. It may be helpful at this point to identify the principal ones; it being understood, of course, that this description does not limit the invention to those embodiments of the application described.

The principal novel products of this invention S2/S3, S3/S2, S2-subunit segments and S3-subunit segments (S2-segments and S3-segments), peptides related to such subunits and segments, antibodies to such subunits and segments, and analogs of these materials.

The principal novel processes of the invention relate to the use of antibodies to PT, the B-oligomer, S2/S3, S3/S2 S2- and S3-subunits, S2- and S3- segments, peptides related to such products, and analogs of all such products.

A further important aspect of the invention is the genes used to produce the proteins and peptides used in the invention. These genes are produced by known methods and may be used in standard procedures to express the desired proteins and peptides. These methods include, for example, producing the desired gene, inserting it in a plasmid, utilizing the plasmid to transform a bacteria, e.g. *E. coli*, growing the bacteria under conditions such that it will express the desired product and, finally, isolating the product.

The various embodiments of the invention which may be realized from the recognition that S subunits and subunits of certain selectins are structurally related and of the important consequences thereof will now be discussed.

1. S2, S3, S2/S3, S3/S2, S-segments, peptides and analogs of these products and mixtures thereof competitively inhibit cellular recognition of selectins and thereby inhibit the inflammatory process or lymphocyte homing.

Products of this invention which contain CRD's act like selectins because they (a) competitively inhibit leukocyte adherence to selectin coated surfaces and (b) mimic the ability of selecting, once bound to the leukocytes to stimulate expression of the integrin CR3 on leukocytes.

FIG. 4A schematically illustrates the fact that certain products of the invention competitively inhibit the adhesion of leukocytes to ELAM or GMP 140. FIG. 4B shows the results of specific competitive assays conducted as schematically illustrated in FIG. 4A. In the study, the proteins PT, B-oligomer, S2, S3, S2/S3 and S3/S2 were taken up in an isotonic buffered tissue culture medium to a concentration of 50 ug/ml and the ability of each of them to inhibit adhesion of neutrophils to ELAM or GMP140 was determined as described by Wright et al *J. Exp. Med.* 158:2016 (1983). The buffer was employed as the control and each protein studied was compared to the control for the ability to decrease adhesion capacity. The native PT, as will be seen, was 60% inhibitory for ELAM and 30% inhibitory for GMP140, S2 and S3/S2 were more effective against GMP140 while S3 and S2/S3 were more effective against ELAM.

It will be seen from 4C that this inhibition is dose related.

As will be seen, there was no increase of CR3 with the buffer compared to the positive control fNLLP. The most effective protein was S3. The least effective was S4. The other products are intermediate in activity. The analog S2/S3 behaved like S3 and S3/S2 behaved like S2.

Figure 3:
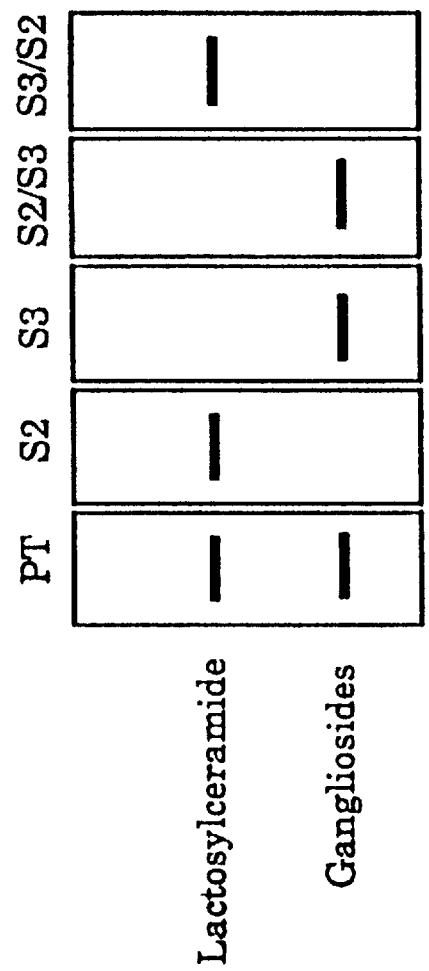
Figure 4A:
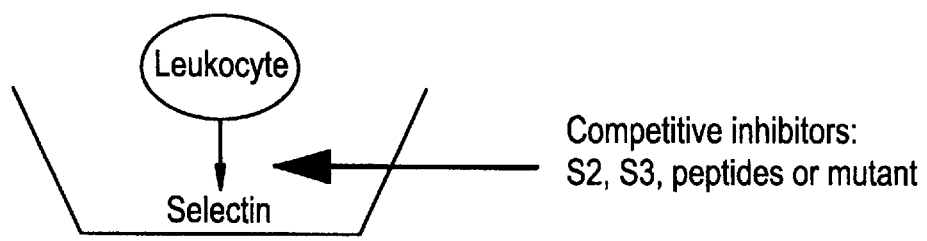
FIG. 4D shows inhibition of neutrophil adherence ELAM by a series of S2 analogs. Analogs with the indicated substitutions at residues $Glu^{43}$, $Tyr^{44}$, $Arg^{50}$ and $Gly^{51}$ (arrows) bind sialylated glycoconjugate (like S3) while the remaining analog proteins either recognize only lactosylaceramide (like S2) or neither carbohydrate.
Figure 4B:
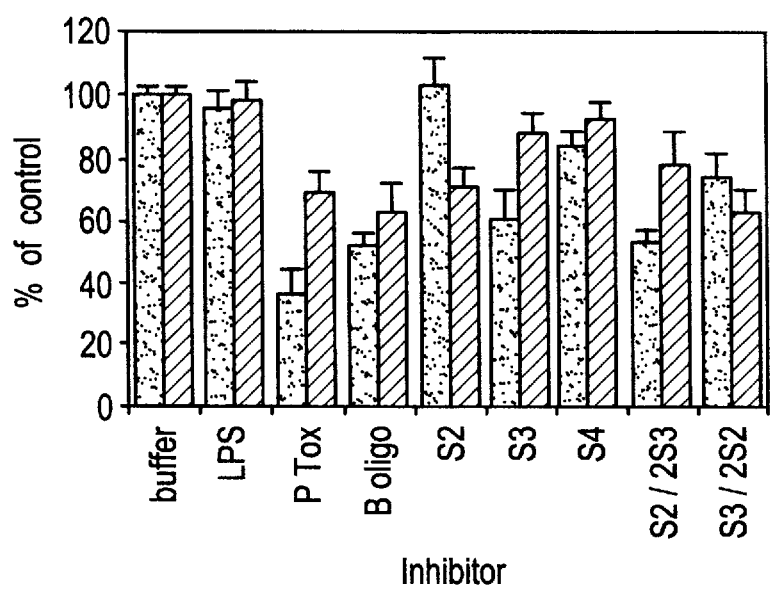
Figure 4C:
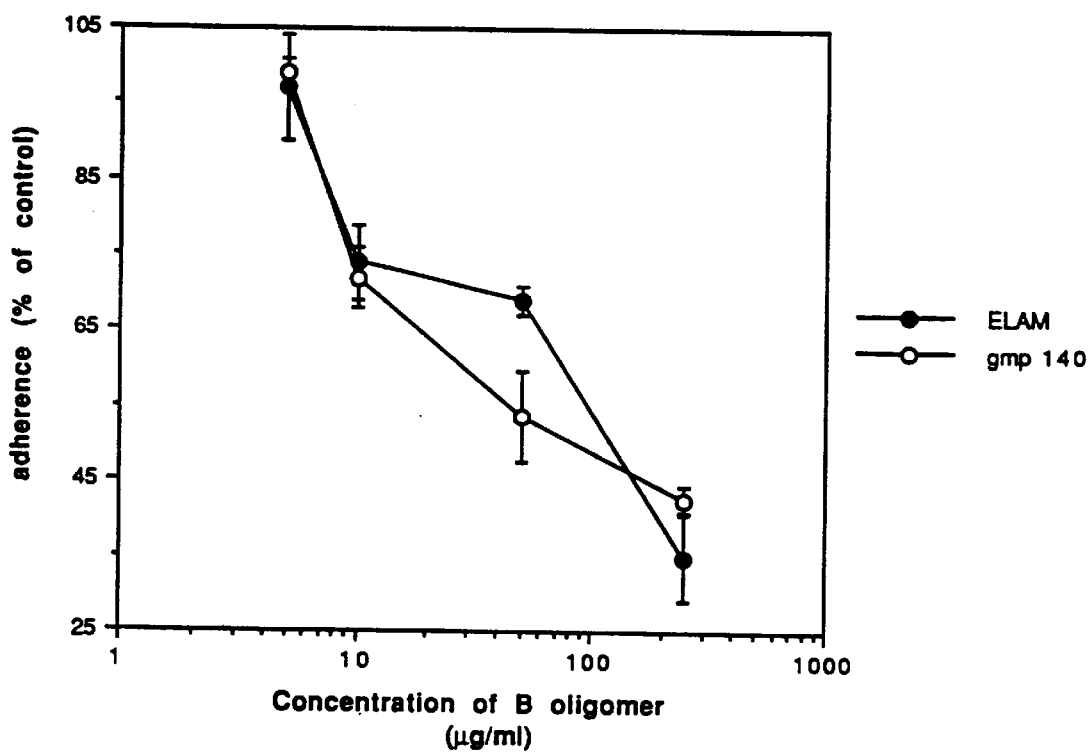
Figure 4D:
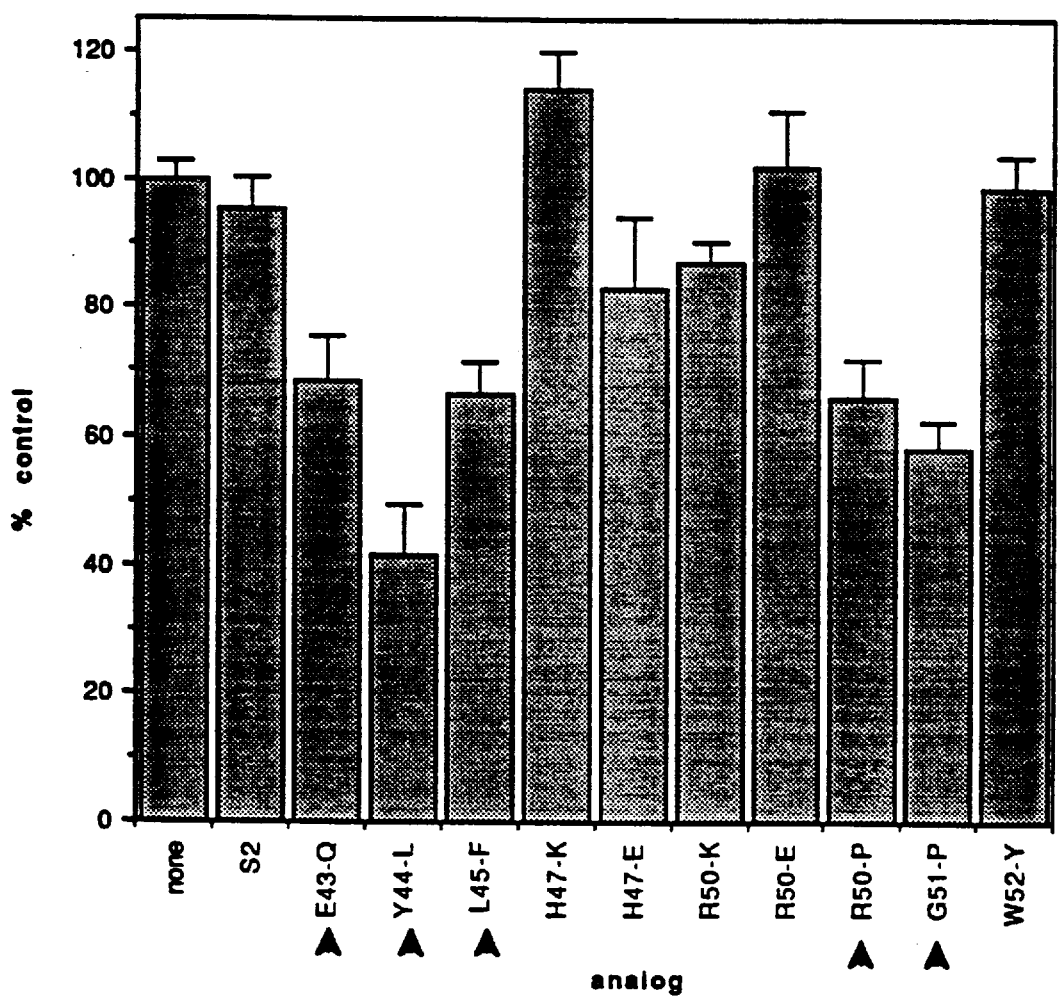
Figure 5A:
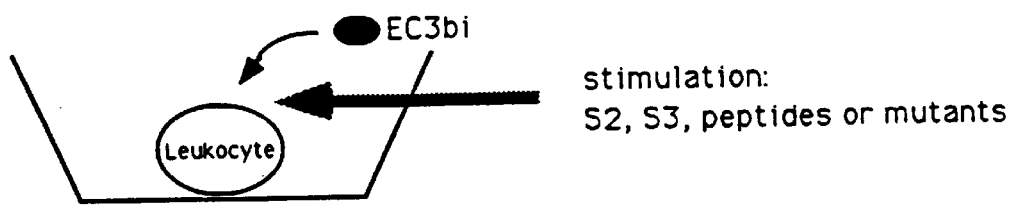
FIG. 5A shows schematically the stimulation of neutrophils to activate CR3 when exposed to certain products of the invention. EC3bi is an erythrocyte coated with the complement component C3bi and is used to detect the presence of CR3 on the surface of a leukocyte according to the procedure of Wright et al (supra).
Figure 5B:
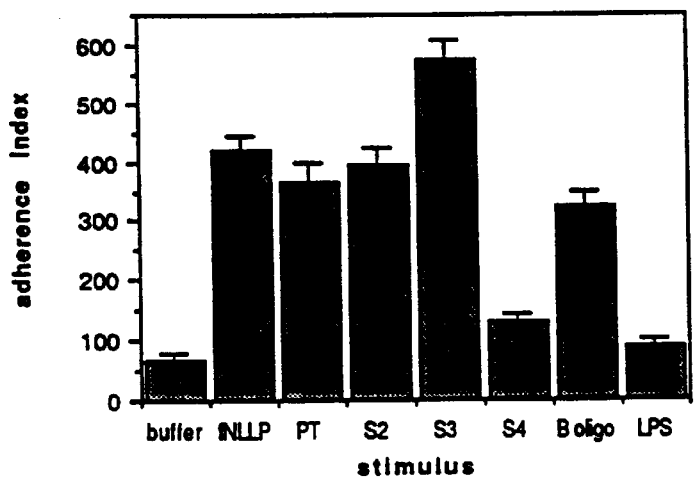
FIG. 5B shows the result of the test schematically illustrated in FIG. 5A. The test was conducted with separate proteins in tissue culture as in the experiment described in connection with the previous figure.

The activities of PT and the other products shown in FIGS. 4 and 5 are characteristic of selectins. Peptides derived from these products will also achieve these desirable results.

FIG. 6A illustrates the operation of the selectin-like in vivo activity of the products discussed.

The left side of the figure shows the passage of a leukocyte through the endothelium. The right side of the figure shows that S-subunits, segments S2/S3 or S3/S2 in the blood stream react with and adhere to the receptor carbohydrate of a leukocyte and prevent the leukocyte from reacting with ELAM on an endothelial cell, thereby inhibiting the inflammatory sequelae of the opening of the endothelium as explained in more detail below.

Figure 6B:
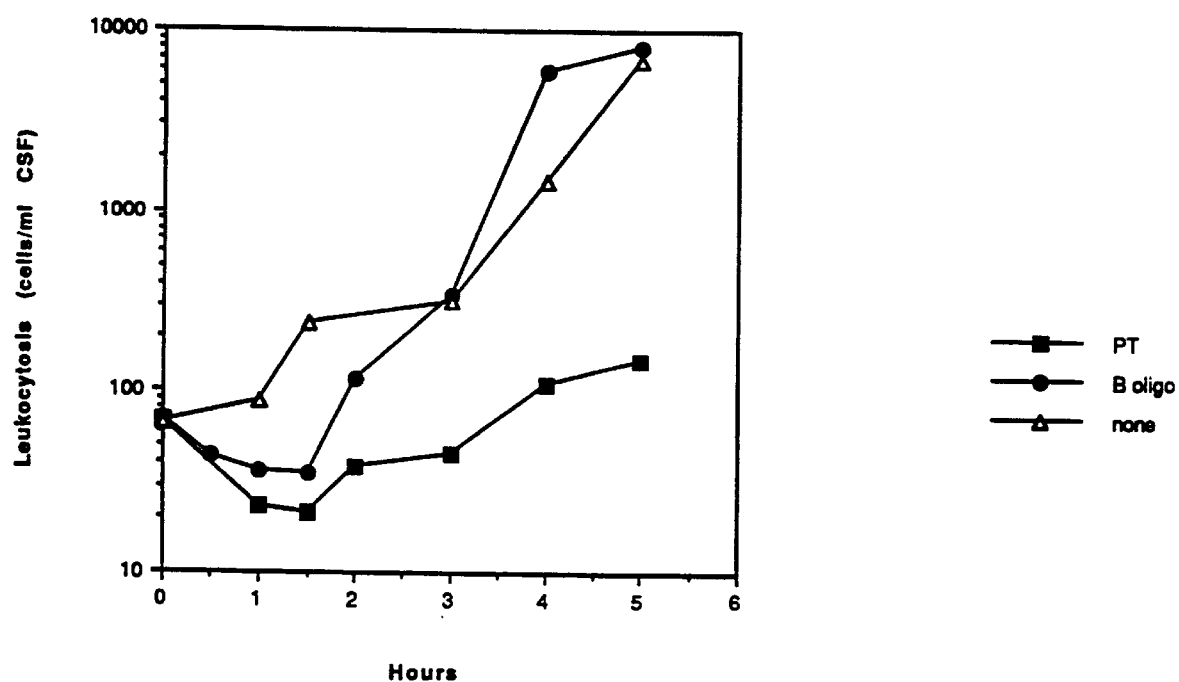

This is shown experimentally in FIG. 6b. In the experiments rabbits with established pneumonococcal meningitis received intravenous PT or B-oligomer. Both treatments decreased the accumulation of leukocytes in cerebrospinal fluid.

2. Antibodies and analogs of the invention may be employed to block ELAM on endothelial cells and inhibit the inflammatory process.

Leukocytes, such as lymphocytes, monocytes, and polymorphonuclear leukocytes (PMN), circulate in the blood and do not adhere to the endothelium. In general, there are two instances in which the leukocytes exit the circulation. The first is the normal lymphocyte homing or trafficking, and the second is the abnormal instance of an inflammatory state in the tissues. Normally, during cellular maturation, lymphocytes enter the lymph tissues such as lymph nodes, lung and gut, exiting from the blood stream through high endothelial venules in the process called lymphocyte homing. For this process, the lymphocytes use the selectin hLHR discussed above to recognize endothelial lymphatic tissue. In the second procedure, the introduction into the tissue of (1) an infectious agent, (2) fragments that result from the death of an infectious agent, or (3) another inflammatory substance, induce leukocytes, such as PMN to bind to the endothelium and then migrate into the tissues. This is a process in which the leukocyte initially binds to receptors on the endothelia including ELAM and GMP140. This permits the leukocyte, in the second step, to move from the ELAM and GMP 140, through the junctions and into the tissue. Since leukocytes can recognize and kill many infectious agents, the passage of leukocytes through the endothelium and into the tissue is a protective mechanism. However, in many disease circumstances, leukocytes react in an exaggerated and deleterious fashion. They may bind so avidly to endothelium as to occlude blood flow. Once in the tissues, they secrete proteases, reactive oxygen intermediates, and other toxic molecules which not only kill infectious agents, but also can result in extensive tissue damage. In addition, they trigger release of inflammatory mediators that alter vascular tone and permeability, and recruit additional leukocytes to the site, thus perpetuating inflammation.

Antibodies to PT, the B-oligomer of PT, S-subunits, S-segments, peptides and analogs will react with and bind to ELAM. Typical antibodies of this nature which cross react with ELAM on dot blots are listed above. If this binding occurs on the endothelial cells, it could inhibit the attachment of leukocytes to the vessel wall thus reducing the numbers of leukocytes or other inflammatory agents which will migrate into the tissue.

The left side of FIG. 7 illustrates the normal adhesive reaction between a carbohydrate receptor on a leukocyte and ELAM of the endothelium. After this reaction as shown by the arrow, a cell junction opens and the leukocyte moves from ELAM into the tissue.

The right side of the sketch shows that the presence in the blood stream of the products discussed herein prevents this reaction because the antibodies react with and block the selectin region of the endothelial cell. This has the effect of preventing the adhesion of the leukocyte to the endothelium so that the leukocyte cannot pass through the endothelium into the tissue. Effectively, the prevention of adhesion inhibits the inflammatory response.

An infection in which leukocyte mediated damage contributes to morbidity and mortality of disease is bacterial meningitis. Depending upon the infecting organism, thirty percent of the cases of patients having meningitis per year die despite sterilization of the infection by antibiotics. Over fifty percent of survivors have permanent severe sequelae such as paralysis, deafness, and learning disabilities. Obviously, the prevention and/or diminishment of such damage would greatly enhance the quality of life for the survivors of this disease.

Figure 7B:
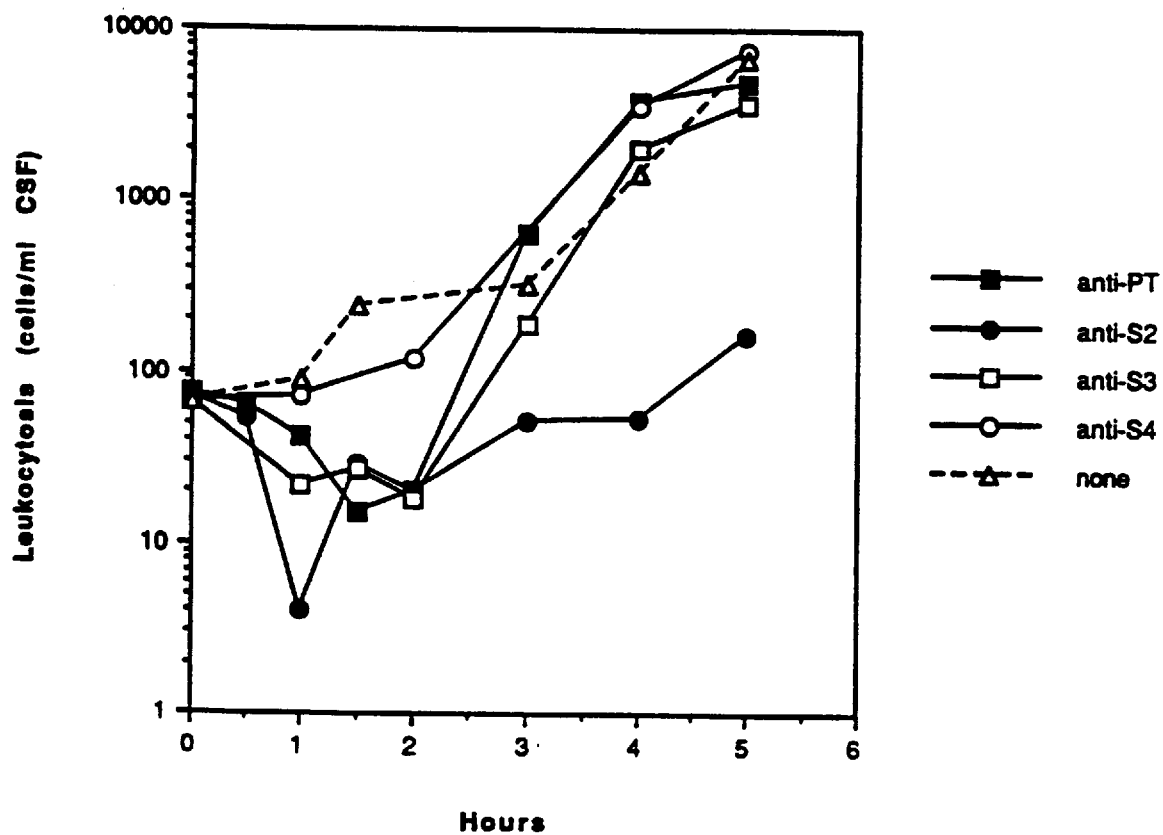

FIG. 7B illustrates the use of anti S-segment antibodies to decrease the inflammation in a rabbit model of meningitis. Rabbits with established pneumonococcal meningitis received antibodies to intact PT or PT subunits: S2:3A12, S3:6F8 and S4:9C6. Control animals and those receiving anti-S4 developed a brisk leukocytosis in cerebrospinal fluid. In contrast, those treated with polyclonal anti-PT, anti-S3 or, particularly, anti-S2 showed significantly fewer leukocytes in cerebrospinal fluid.

Activated leukocytes also contribute to cerebral edema and blood-brain barrier injury. Neutropenic animals (animals in which the leukocytes have been artificially diminished) have been found to have improved survival rates in experimentally induced disease. A high amount of inflammation in the subarachnoid space correlates directly with a poor outcome of disease. Inhibition of the accumulation of leukocytes in cerebrospinal fluid directly correlates with reduced morbidity and mortality of experimental pneumococcal meningitis and of *Haemophilus influenzae* meningitis and bacteremia in children.

Clearly, an agent which would inhibit the lymphocyte homing modulation of immune response, movement of metastatic cells to lymph nodes or the influx of leukocytes into infected sites would be a therapeutic tool of immense value particularly if non-leukocyte mediated defense systems are left functionally intact. It would further be beneficial to block leukocyte diapedesis only at inflamed sites and not at other sites throughout the body. Thus treatment directed at inflammed endothelia would be advantageous over that directed to leukocytes. For example, ELAM recruits leukocytes to skin. Therefore anti-ELAM antibodies would inhibit acute and chronic inflammation of the skin such as psoriasis, dermatitis and the like.

The use of antibiotics magnifies the deleterious effects of inflammation during infectious diseases. This is due to the mechanism by which such agents exert their antiinfective effects. For example, following the administration of a beta-lactam antibiotic (or another cell-wall directed antibiotic), the bacteria disintegrate due to lysis by the antiinfective agent. The resulting fragments of bacteria initiate a dramatically enhanced inflammatory response. Earlier research has indicated that inhibition of this enhanced level of inflammation correlates with reduced morbidity and mortality, Tuomanen et al., *J. Infect. Dis.*, 155, 985–990 (1985) and Kadurugamuwa, *Program and Abstracts of the 27th ICAA Meeting*, p. 205 (1987). In pneumococcal meningitis, for instance, mortality can be directly correlated with the amount of meningeal inflammation, McAllister et al., *J. Infect. Dis.*, 132, 355–360 (1975). Thus, a method of dampening inflammation during the course of therapy with an antibiotic would be advantageous in treating infections, particularly meningitis, septic arthritis, and endophathalmitis.

The process of this invention will be useful in treating inflammation caused by any of a variety of infective agents, including gram-positive and gram-negative bacteria as well as viruses and fungi. Particularly targeted infections are those which are susceptible to treatment with beta-lactam antibiotics, or antiviral agents such as *Haemophilus influenzae* B; *N. meningitidis* b; Pneumococci, e.g., *Streptococcus pneumoniae*; *Escherichia coli*; *Staphylococcus epidermidus*; *Staphylococcus aureus*; group B Streptococci; Salmonella; *Bacillus subtillis*; *Pseudomonas aeroginosa*; and Herpes virus.

The infected tissue which is the target of the present invention can be tissue in any body site susceptible to inflammation caused by the above-described infective agents. The method of the present invention is, however, particularly adaptable to the treatment of infected tissue of the central nervous system, lung, kidney, joints, endocardium, eyes and ears, with the treatment of the cerebrospinal fluid and articular fluid being highly preferred embodiments.

One particularly susceptible tissue for which the present invention is uniquely suited is the tissue of the central nervous system. The vascular endothelium in the brain is morphologically different from the in other tissues in that endothelial cells are jointed by tight junctions thereby creating a blood-brain barrier which prevents molecules the size of proteins from passing from blood into the cerebrospinal fluid. The products of this invention are particularly useful in the treatment of meningitis infections, including those arising from pneumococci, *Haemophilus influenzae* B, *N. meningitidis* b and *Escherichia coli*, group B Streptococcus and Staphylococci.

Additionally, the ingress of leukocytes into articular fluid can be prevented by administration of a therapeutic amount of one or more antibodies of the present invention. In cases where the inflammation of an infection migrates to the joints, e.g. arthritis, this method can be utilized to alleviate the inflammation by preventing the ingress of leukocytes into the articular fluid.

The process of this invention is useful in the control of inflammation arising from substantially any source including, for example autoimmune disease.

The peptides, antibodies and other products of the invention can also serve as carriers for targeting therapeutic agents to selectin-bearing cells in mammals. For this purpose, the therapeutic agent will be chemically bonded to the peptide or antibody substrate and the combined product administered to the patient in need of such treatment. These therapeutic agents include, for example coagulation cascade modifiers or immunomodulators such as cytokines. They may include also immunotoxins such as Pseudomonus exotoxin A or ricin attached to an anti-S-subunit antibody of the invention to produce products capable of binding to selectins on leukocytes or vascular endothelium (for example, lymph nodes or skin) for the treatment of diseases such as malignancies. Procedures for combining such therapeutic agents with peptides and antibodies are well known. One example of this procedure, provided only as a means of illustration, is the use of a therapeutic agent attached to an anti-S-subunit antibodies which bind ELAM to seek out inflammed skin. Peptides of the invention, their analogs and other products of the invention having like activity such as S2 and S3 segments will deliver the therapeutic agent to circulating cells. Antibodies of the invention and their analogs will deliver the therapeutic agent to eukaryotic cells.

In certain patients, a potential problem with the use of a murine anti-S-subunit monoclonal antibody, such as those employed in this invention exists since the patient may generate an immune response against a murine monoclonal antibody. This effect may be ameliorated or obviated by using active fragments of the monoclonal antibody so as to minimize the amount of foreign protein injected. Another alternative is to employ genetic engineering techniques to make a chimeric antibody in which the binding region of the murine anti-S-subunit antibody is combined with the constant regions of human immunoglobin.

A further method of the present invention is that of reducing or eliminating inflammation in an infectious disease caused by the administration of an antiinfective agent for that disease which comprises the simultaneous administration of an effective amount of antiinfective agent and an effective amount of an anti-S-subunit antibody or an active fragment thereof to a patient in need of such therapy. As explained above, due to the mechanism of their therapeutic activity, antiinfective agents, and particularly beta-lactam antibiotics, cause additional inflammation as a result of their therapeutic effect.

The term "simultaneous administrations" as used herein means that therapeutic amounts of the antiinfective agent and the anti-S-subunit antibody are administered within a time period where they influence each other. Thus the anti-infective agent may be administered at the same time or before or after the antibody.

Reduction or elimination of inflammation in infectious diseases results in a diminution of the neurological damage that usually accompanies such infections. Since several of the products the antibodies of this invention possess the unique ability to block movement of leukocytes across the blood-brain barrier, they are uniquely suited to treat infections where the causative infective agent is *Haemophilus influenza* B, *N. meningitidis* b, or a pneumococci such as *Streptococcus pneumoniae*. Such infections are generally treated with an aminoglycoside such as gentamicin or a beta-lactam antibiotic such as a penicillin or cephalosporin.

Due to the ability of anti-S-subunit antibodies peptides and other products of this invention to reduce or eliminate the inflammation in an infectious disease caused by the administration of an anti-infective agent, the therapeutic agent can be combined in a single unit dosage form with the anti-infective agent for convenience of administration. Such dosage form is most preferably an intravenous dosage form since most anti-infective agents, particularly the beta-lactam antibiotics, are available in a suitable chemical form for administration via the intravenous route. Typically, the anti-infective agent and one or more antibodies or other agent of the invention can be combined a single ampoule solution. Where this is not possible, the anti-infective agent and the selected product of this invention can be packaged separately and mixed just prior to injection. Administration can likewise be via a mixture with any standard intravenous solution, i.e., normal saline.

The amount of anti-infective agent in the dosage form is dependent upon the particular anti-infective agent being utilized and the particular infection being treated. The amount of the antibody utilized in dosage form can range from about 1 to about 1,000 mg, with 10–100 mg per dosage unit being highly preferred. Dosages can be administered one to four times daily, with continued therapy for as long as the infection persists.

3. S2, S3, S2/S3, S3/S2, S-segments, peptides and analogs of these products and mixtures thereof may function as vaccines.

S-subunits and segments thereof play a crucial role in the adherence of BP to leukocytes and to cilia of the respiratory tract. See Table I page 15. Antibodies to many epitopes on the S-subunit and other products employed in this invention will prevent such adherence by blocking the BP thereby denying the bacteria the opportunity to adhere to leukocytes or cilia and thereafter establish infections.

Products of the invention may, therefore, be employed as vaccines. Upon administration to mammals in need of such vaccines, they will generate antibodies in an amount which will be effective to inhibit the adherence interaction of BP with eukaryotic cells including leukocytes and cilia. Typically, the agent of the invention will be administered with a pharmaceutically acceptable carrier.

Figure 8:
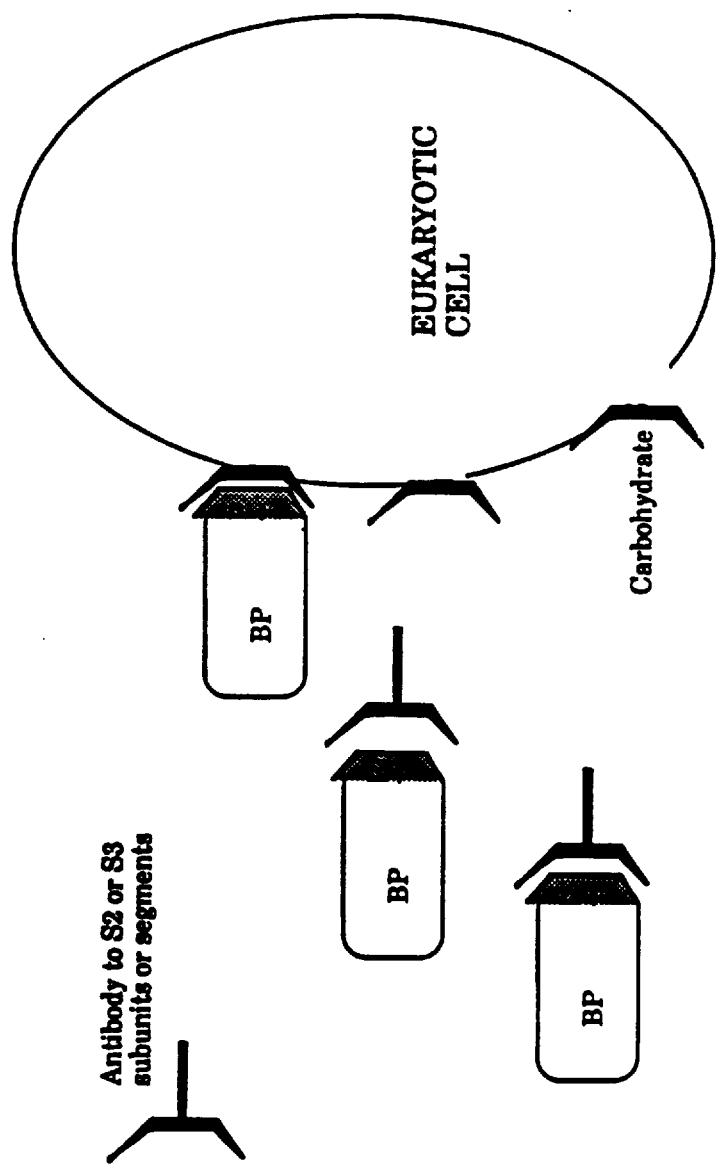

FIG. 8 shows how antibodies to S-subunit or S-segments peptides and other products of the invention act as vaccines by inhibiting adherence of BP to eukaryotic cells.

It will be apparent to the skilled artisan that some of the same antibody vaccines used to protect against BP infections as explained in Item 3 may also cross react with natural selectins on host cells. This latter activity might be regarded as a toxic reaction for a product intended for use as a vaccine. Accordingly, it is preferred for the production of vaccines to select peptides generating antibodies which will block binding of BP to eukaryotic cells but will not react with selectins. Such peptides will be selected from amongst the peptides of the invention which do not mimic the activity of the CRD region of S-subunits.

DISCUSSION OF PEPTIDES

The segments of S2 and S3 from positions 32 to position 45, as shown of FIG. 1 are especially fruitful sources of peptides for the practice of this invention. In fact, peptides containing the boxed conserved residues VA and YL for any of the segments shown in the figure are especially useful. The VA/YL core peptides may be expanded upstream towards the amino end or downstream towards the carboxyl end and still retain their utility providing that they contain the VA and the YL residues and the amino acid residue at the third or fourth position upstream of the Y residue is E or D. In preferred products the first amino acid residue upstream of the Y is E, D or T. Thus, as illustrated in the figure, useful peptides may contain from 12 to about 35 amino acid residues. Some variation from this range can be tolerated, as will be readily apparent from this description of the invention. The presently preferred peptides contain from about twelve to about twenty amino acid residues. These are preferred since they may be readily synthesized in pure form by solid phase techniques.

In the figure, certain of the segments are shown with blank spaces to emphasize the unexpected degree of homology between peptides derived from prokaryotic and eukaryotic sources. Of course, there are no empty spaces in the actual products. The prokaryotic peptides of the invention may be made to more closely resemble selectin peptides by deleting $S^{38}$ and/or $Q^{42}$ from the S2 segment or $N^{38}$ and/or $Q^{32}$ from the S3 segment. The same effect can be achieved by inserting amino acids in the blank spaces in the selectin segments. Such additions or deletions can be made without disturbing the alignment of the VA and YL in the prokaryotic and eukaryotic peptides.

The same alignment may also be maintained by changing the position of the blank space in ELAM between the VA and the YL residue. This will be clear from a study of the following possible VAIQNKE-EI (SEQ ID NO:1)
VAIQNK-EEI (SEQ ID NO:2)
VAIQN-KEEI (SEQ ID NO:3)
VAIQ-NKEEI (SEQ ID NO:4)
VAI-QNKEEI (SEQ ID NO:5)
VA-IQNKEEI (SEQ ID NO:6)

based on the VA------EI sequences at positions 27 through 37 in the ELAM segment shown in the figure.
Original
VAIQNKE-EI
VAIQNK-EEI
VAIQN-KEEI
VAIQ-NKEEI
VAI-QNKEEI
VA-IQNKEEI A similar result is achieved by deleting one amino acid residue from the VA------EL section of the S3 segment shown in the figure.

VAELRGNAEL (SEQ ID NO:7)
VAELRGN-EL (SEQ ID NO:8)
VAELRG-AEL (SEQ ID NO:9)
VAELR-NAEL (SEQ ID NO:10)
VAEL-GNAEL (SEQ ID NO:11)
VAE-RGNAEL (SEQ ID NO:12)
VA-LRGNAEL (SEQ ID NO:13)

Original
VAELRGNAEL
VAELRGN-EL
VAELRG-AEL (SEQ ID NO:9)
VAELR-NAEL (SEQ ID NO:10)
VAEL-GNAEL (SEQ ID NO:11)
VAE-RGNAEL (SEQ ID NO:12)
VA-LRGNAEL (SEQ ID NO:13)

Similar considerations will apply to other sections of the segments shown. The important point is that the peptides to be useful should have the VA, E or D, and YL residues as defined and shown in the figure and that the alignments should be maintained when making any deletions or addition.

Additions and deletions can be made in other sections of the segments, and one or more of the amino acid residues shown in the figure can be replaced so long as the changes do not disturb the alignments. Thus, for example, in larger peptides containing the appropriate VA, E or D and YL configuration, the amino acid residues between C and H or YL and S can be changed.

With the foregoing in mind, the preferred peptides and analogs of this invention can be defined as peptides containing at least 12 and up to about 35 amino acid residues having or containing a segment represented by the formula:SEQ ID NO:14

VAXXXXXXXZXXXYL wherein X represents any amino acid residues, each being independently selected; Z is E or D amino acid residues, and deletion or addition derivatives thereof in which no more than one X residue on either or both sides of the Z residue has been added or deleted.

Products in which the first amino acid upstream of the Y residue are presently preferred.

A number of useful peptides within the scope of the invention have been proposed. These include: SEQ ID NO:15–28
VAIQNKEEIEYLNSILSYS (SEQ ID NO:15)
THLVAIQNKEEIEYL (SEQ ID NO:16)
TLVAIQNEEIEYL (SEQ ID NO:17)
VAIQNKAEIEYLEKTLPFS (SEQ ID NO:18)
TDLVAIQNKAEIEYL (SEQ ID NO:19)
VAELRGSDGLQEYLRHVTRGWS (SEQ ID NO:20)
QNKNEIDYLNKVLPYYS (SEQ ID NO:21)
RALTVAELRGSGDLQEYL (SEQ ID NO:22)
ALTVAELGSGDLQEYL (SEQ ID NO:23)
VAELRGNAELQTYLRQITPGWS (SEQ ID NO:24)
RALTVAELRGNAELQTYL (SEQ ID NO:25)
ALTVAELGNAELQTYL (SEQ ID NO:26)
TVAELRQNELQTYLRQITPGWSITGLYDTVAI (SEQ ID NO:27)
TVAELRGSDLGEYLRHVTRGWSI (SEQ ID NO:28)

Typically, they were prepared by either the t-BOC or FMOC solid phase method. The procedures are as follows:

t-BOC METHOD (t-BOC) peptides were synthesized on an Applied Biosystems model 430 Peptide synthesizer utilizng standard t-BOC/Dicyclohexylcarbodiimide/Dichloromethane coupling chemistry. Syntheses were performed at the 0.5 mmol scale using standard t-BOC amino acids with the following side chain protecting groups: Arg(Toluenesulfenyl), Asp (OBenzyl), Cys(4-Methylbenzyl), Glu(OBenzyl), His (Dinitrophenyl), Lys(2-chlorobenzyloxycarbonyl), Ser (Benzyl), Thr(Benzyl), and Tyr(2-bromobenzyloxycarbonyl). All histidine, glutamine, arginine and asparagine residues were double coupled. The relevant c-terminal amino acid coupled 4-(carboxamidomethyl)benzyl ester linked polystyrene (PAM) was used as the starting resin. The final resin was dried and subjected to Hydrofluoric acid cleavage and deprotection. The cleaved, dried peptide was purified to greater than 90% purity by HPLC using a Vydac C4, 300 angstrom pore size, 1 cm×25 cm reverse phase column with binary gradients of 0.05% TFA/Acetonitrile and 0.1% TFA/Water and lyophilized. Amino acid compositions were verified on an Applied Biosystems model 420A/130A/920A Amino Acid compositions system.

FMOC METHOD

9-Fluorenylmethoxycarbonyl(Fmoc) peptides were synthesized on Applied Biosystems (ABI) model 431 Peptide synthesizer utilizing standard 1-Hydroxybenzotriazole/N-Methylpyrrolidone coupling chemistry. Syntheses were performed at 0.25 mmol scale using standard Fmoc amino acids with the following side chain protecting groups: Arg(4-methoxy-2,3,6-trimethylbenzenesulfonyl), Arg(2,2,5,7-pentamethylchroman-6-sulfonyl), Asp(O-t-Butyl), Cys(t-Butyl), Glu(O-t-Butyl), His(Trityl) Ser(t-Butyl), Thr(t-Butyl), and Tyr(t-Butyl). All histidine, glutamine and asparagine residues were double coupled whenever they occurred after the first eight amino acids from the carboxy terminus. 4-Hydroxymethylphenoxy linked polystyrene unloaded polymer was used as the starting resin. The last N-terminal Fmoc protecting group was removed while the resin was still on the synthesizer. The final, dried peptide resin was cleaved from the resin and deprotected in one of the following mixtures. If the peptide contained Arg or Met: 1.) 10 ml Trifluoroacetic acid(TFA): 0.75 g Phenol: 0.25 ml ethanedithiol(EDT) or b-Mercaptoethanol (bME): 0.5 ml Thioanisole: 0.5 ml Water. If the peptide contained Trp or His: 2.) 9.5 ml TFA: 0.25 ml EDT or bME: 0.25 ml Water. If none of the above amino acids were present: 3.) 9.5 ml of TFA: 0.25 ml Water. The cleavage mixture was stirred for approximately 1–3H. The resin was filtered through a scintered glass funnel with washes of methylene chloride and the filtrate was concentrated by roto-evaporation to approximately 5 ml. The peptide was precipitated with cold ether and isolated on a scintered glass funnel, washed with additional cold ether and dried in a vacuum dessicator. The resultant peptide was purified to greater than 90% purity by HPLC using a Vydac C4, 300 angstrom pore size, 1 cm×25 cm reverse phase column with binary gradients of 0.05% TF/Acetonitrile and 0.1% TFA/Water and lyophilized. Amino acid compositions were verified on an Applied Biosystems model 420A/130A/920A Amino Acid compositions system.

Peptide number 3 is a deletion peptide of peptide number 2 from which the first histidine residue has been deleted. Peptide 8 is a deletion peptide of peptide 7 formed by removal of both arginine residues.

Table 2 records the results of some of the studies conducted with preferred products of the invention.

On the left is a list of peptides derived from the designated selectin or S subunit. They are presented to show how they constitute overlapping fragments of the designated CRD. Spaces are inserted to emphasize alignment and are not present in the actual peptide. on the right is the activity of the peptide (at 1 mg/ml) in 3 assays of selectin function.

Assay 1 is inhibition of adherence of enutrophils to ELAM-coated surfaces as described in connection with FIG. 4. Values ±20% inhibition are significant.

Assay 2 is inhibition of adherence of a neutrophil to a monolayer of endothelial cells as described by Lo et al *J. Exp. Med.* 173:1493–1500 (1991). Values ±50% inhibition are significant.

Assay 3 measures upregulation of integrins on the surface of a neutorphil as described in FIG. 5. Values ±50% are significant.

NT=not tested

Partially purified $S_2$ protein inhibited in Assay 1 to Table 2 by 36% while $S_3$ inhibited by 27%. As will be seen from the Table all peptides (except 8) conforming to the VAxxxxxxZxxxYL motif SEQ ID NO:14 were active in Assays 1 or 2 which measure adherence of leukocytes to selectins or endothelial cells bearing selectins. Peptides 7 and 11 are active and illustrate that removal of one amino acid from the string of x-residues in the motif (as indicated by the space in the sequence) is still permissive for activity.

Single amino acid substitutions may or may not be permissive as illustrated in FIG. 4D where a number of amino acid substitutions are designated. Those indicated by arrows have the ability to recognize ganglio sides (like S3) and are active like S3. Loss of carbohydrate recognition abolishes activity.

In FIG. 4D, the notation E43-Q indicates that the q amino acid residue at position 43 has been substituted by an E amino acid residue. The other notations have similar meanings.

It is further noted from Table 2 that 7 of 8 peptides containing the VA . . . YL motif (peptides 2, 3, 4, 5, 7, 8, 9, 11) have a second property of selectins shown by assay 3, i.e, the ability to upregulate integrins on leukocytes. One

TABLE 2

| | % of inhibition ASSAY 1 | % of inhibition ASSAY 2 | # of cells ASSAY 3 |
|---|---|---|---|
| ELAM | | | |
| 1. SEQ ID NO:29 KEEIEYLNSILSYS | 0–2 | NT | 73 |
| 2. SEQ ID NO:15 VAIQNKEEIEYLNSILSYS | 22–52 | NT | 71 |
| 3. SEQ ID NO:30 TLVAIQNKEEIEYL | NT | 80 | 243 |
| hLHR | | | |
| 4. SEQ ID NO:31 VAIQNKAEIEYLEKTLPFS | 23–31 | NT | 163 |
| 5. SEQ ID NO:19 TDLVAIQNKAEIEYL | NT | 80 | 104 |
| S3 | | | |
| 6. SEQ ID NO:32 AELQTYLRQITPGWS | 0–18 | NT | 122 |
| 7. SEQ ID NO:26 ALTVAEL GNAELQTYL | | | |
| GMP140 | | | |
| 8. SEQ ID NO:33 VAIQNKNEIDYLNKVLPYYS | 3–14 | NT | 113 |
| S2 | | | |
| 9. SEQ ID NO:34 VAELRGSGDLQEYLRHVTRGWS | 22–33 | NT | 18 |
| 10. SEQ ID NO:35 GDLQEYLRHVTRGWS | 0–14 | NT | 104 |
| 11. SEQ ID NO:36 ALTVAEL GSGDLQEYL | NT | 80 | 232 | such peptide, peptide 9 from S2, does not share this property. The dissociation of activity in assays 1 and 2 from assay 3 is desirable since inhibition of leukocyte adherence without the activation of integrin—mediated leukocyte adherence would improve anti-inflammatory activity. This is consistent with the greater antiinflammatory activity of anti-S2 antibody in vivo (FIG. 7B) as compared to the anti-S3 antibody. To further illustrate the importance of the VA and YL regions of the preferred peptide motif, each was deleted separately from the S3 protein SEQ ID NO:37 according to the scheme illustrated below:

```
            Deletion 1       Deletion 2
                ↓                ↓
    ... TRALT VAEI  RGNA ELQTYLRO ITP ...
``` whereas the intact S3 protein inhibited leukocyte adherence to ELAM coated surfaces by ±70% at 50 ug/ml, S3 with deletion 1 SEQ ID NO:38 inhibited by only 16% and S3 with deletion 2 SEQ ID NO:39 inhibited by only 15%.

The products of the invention may be provided as parenteral, oral or other compositions including, for example nasal and topical compositions, for injection, infusion, or other procedures; such compositions comprising a prophylactically effective amount of the selected therapeutic agent and a pharmaceutically acceptable carrier. They can, for example be suspended in an inert oil, or in alum or other suitable adjuvant. Alternatively, they can be suspended in an aqueous isotonic buffer solution at a pH of about 5.6 to 7.1. Useful buffers include sodium phosphate-phosphoric acid.

The desired isotonicity may be accomplished using sodium chloride or other pharmaceutically acceptable agents such as dextrose, boric acid, sodium tartrate, propylene glycol or other inorganic or organic solutes. Sodium chloride is preferred particularly for buffers containing sodium ions.

If desired the compositions may be thickened with a thickening agent such as methyl cellulose. They may be prepared in emulsified form, either water in oil or oil in water. Any of a wide variety of pharmaceutically acceptable emulsifying agents may be employed including, for example acacia powder, or an alkaryl polyether alcohol sulfate or sulfonate such as a Triton.

The therapeutically useful compositions of the invention are prepared by mixing the ingredients following generally accepted procedures. For example, the selected components may be simply mixed in a blender or other standard device to produce a concentrated mixture which may be then be adjusted to the final concentration and viscosity by the addition of water or thickening agent and possibly a buffer to control pH or an additional solute to control tonicity.

The dosage and method of administering the products of the invention may be varied due to patient condition, the result sought to be achieved and other factors readily evaluated by the attending physician or veterinarian. For example, while the presently preferred method of administering vaccines of the invention is parenteral administration, certain of them will be administered orally in a pharmaceutically acceptable oral carrier.

The peptides of this invention will be valuable for quality control procedures in the production of BP and other vaccines, for example antiviral or antibacterial vaccines to eliminate components generating antibodies which react with selectins. Such peptides may be employed to test for the presence of antigens in the vaccine having the ability to generate toxic antibodies. For example, anti-pertussis vaccines based on S-subunits or fragments thereof many generate antibodies reactive with ELAM on the endothelial surface and open the cell functions to penetration by unwanted substances or otherwise generate an inflammatory response.

To test for such potential toxicity, the candidate vaccine antigen will be employed to immunize an animal such as a rabbit. The antiserum from the immunized animal will be used to overlay human tissue slices or another surface coated with a selectin or a selectin mimicking peptide. Binding of the testing antibody to the tissue section, or the peptide indicates that the vaccine antigen produces antibodies which cross react with ELAM and that the vaccine is toxic.

Any of a variety of tests may be employed to detect the binding of toxic antibodies. Typical tests include radioimmunoassay, enzyme linked immunoassay, as well as, direct and indirect immunofluorescence. These tests may employ competitive and sandwich type assays. Typically, the test will employ detectable labels on an indicator antibody. Useful labels include fluorescent labels such as fluorescein, rhodamine or auramine. Radiosotopes such as $^{14}C$, $^{131}I$, $^{125}I$ and $^{25}S$ may be employed. Enzyme labels which may be utilized

EXAMPLE

| Ingredient | mg/ml |
|---|---|
| Intravenous Formulation I | |
| cefotaxime | 250.0 |
| monoclonal antibody 7E10 | 10.0 |
| dextrose USP | 45.0 |
| sodium bisulfite USP | 3.2 |
| edetate disodium USP | 0.10 |
| water for injection q.s.a.d. | 1.00 ml |
| Intravenous Formulation II | |
| ampicillin | 250.0 |
| monoclonal antibody 6D6 | 10.0 |
| sodium bisulfite USP | 3.2 |
| disodium edetate USP | 0.1 |
| water for injection q.s.a.d. | 1.00 ml |
| Intravenous Formulation III | |
| gentamicin (charged as sulfate) | 40.0 |
| monoclonal antibody 9G8 | 10.0 |
| sodium bisulfite USP | 3.2 |
| disodium edetate USP | 0.1 |
| water for injection q.s.a.d. | 1.00 ml | include, for example, β-glucamidase, β-D-glucosidase, β-D-galactosidase, urease, glucose oxidase plus peroxidase, and acid or alkaline phosphatase. Methods for labeling biological products such as cells, antibodies, antigens and antisera are well known and need not be described.

There are several currently available procedures for detecting these labels including, for example calorimetric, spectrophotometric, fluorospectro-photometric, photometric and gasometric techniques, as well as various instrumental methods of detecting isotopes.

All of these tests involve the formation of a detectable reaction product between the indicator antibody and the test toxic antibody which will react with the ELAM or analogs region on endothelial cells and is generated by an immunological response to a toxic antigen in a vaccine. The indicator antibody, i.e. the labelled antibody, may react directly with the toxic antibody as in the enzyme linked immunoassay procedure (ELISA) or other sandwich type test.

The complete disclosure of all publications cited in this specification is incorporated herein by reference.

The following non-limiting example is given by way of illustration of compositions of this invention.

What is claimed is:

1. A peptide having at least 12 and up to 35 amino acid residues, said peptide

| | |
|---|---|
| VAIQNKEEIEYLNSILSYS | (SEQ ID NO: 15); |
| THLVAIQNKEEIEYL | (SEQ ID NO: 16); |
| TLVAIQNEEIEYL | (SEQ ID NO: 17); |
| VAIQNKAEIEYLEKTLPFS | (SEQ ID NO: 18); |
| TDLVAIQNKAEIEYL | (SEQ ID NO: 19); |
| VAELRGSDGLQEYLRHVTRGWS | (SEQ ID NO: 20); |
| RALTVAELRGSGDLQEYL | (SEQ ID NO: 22); |
| ALTVAELGSGDLQEYL | (SEQ ID NO: 23); |
| VAELRGNAELQTYLRQITPGWS | (SEQ ID NO: 24); |
| RALTVAELRGNAELQTYL | (SEQ ID NO: 25); |
| ALTVAELGNAELQTYL | (SEQ ID NO: 26); |
| TVAELRGSGDLGEYLRHVTRGWSI | (SEQ ID NO: 28); |
| VAIVAIQNKNEIDYLNKVLPYYS | (SEQ ID NO: 40); and |
| TVAELRQNELQTYLRQITPGWSIYGLYDGT | (SEQ ID NO: 41). |

2. A composition comprising the peptide of claim 1 and a carrier.

3. An antibody raised against a peptide selected from the group consisting of:

| | |
|---|---|
| TLVAIQNEEIEYL | (SEQ ID NO:17); |
| VAELRGSDGLQEYLRHVTRGWS | (SEQ ID NO:20); |
| RALTVAELRGSGDLQEYL | (SEQ ID NO:22); |
| ALTVAELGSGDLQEYL | (SEQ ID NO:23); |
| VAELRGNAELQTYLRQITPGWS | (SEQ ID NO:24); |
| RALTVAELRGNAELQTYL | (SEQ ID NO:25); |
| ALTVAELGNAELQTYL | (SEQ ID NO:26); |
| TVAELRGSGDLGEYLRHVTRGWSI | (SEQ ID NO:28); |
| VAIVAIQNKNEIDYLNKVLPYYS | (SEQ ID NO:40); and |
| TVAELRQNELQTYLRQITPGWSIYGLYDGT | (SEQ ID NO:41). |

4. A composition containing a carrier together with the antibody of claim 3.

5. The antibody of claim 3 which is a monoclonal antibody.

6. A composition containing a carrier together with the monoclonal antibody of claim 5.

7. A method of inhibiting the adhesion of circulating cells to endothelia or epithelia in a mammal in need of such inhibition which comprises administration to said mammal a peptide selected from the group consisting of:

| | |
|---|---|
| THLVAIQNKEEIEYL | (SEQ ID NO:16); |
| RALTVAELRGSGDLQEYL | (SEQ ID NO:22); and |
| RALTVAELRGNAELQTYL | (SEQ ID NO:25). |

8. A method of inhibiting the adhesion of leukocytes and endothelia in a mammal in need of such inhibition which comprises administration to said mammal a peptide selected from the group consisting of:

| | |
|---|---|
| THLVAIQNKEEIEYL | (SEQ ID NO:16); |
| RALTVAELRGSGDLQEYL | (SEQ ID NO:22); and |
| RALTVAELRGNAELQTYL | (SEQ ID NO:25). |

9. A composition containing a carrier together with a peptide selected from the group consisting of:

| | |
|---|---|
| THLVAIQNKEEIEYL | (SEQ ID NO:16); |
| RALTVAELRGSGDLQEYL | (SEQ ID NO:22); and |
| RALTVAELRGNAELQTYL | (SEQ ID NO:25). |

10. A method of using the composition of claim 9 for inhibiting adhesion between circulating cells and endothelia or epithelia.

* * * * *

UNITED STATES PATENT AND TRADEMARK OFFICE
CERTIFICATE OF CORRECTION

PATENT NO. : 5,817,617
DATED : October 6, 1998
INVENTOR(S) : Elaine Tuomanen and H. Robert Masure It is certified that error appears in the above-indentified patent and that said Letters Patent is hereby corrected as shown below:

In Claim 1, Column 45, line 33, after the word "peptide" insert

--contains the structure selected from the group consisting of:--

Signed and Sealed this

Twelfth Day of January, 1999

Attest:

Attesting Officer

*Acting Commissioner of Patents and Trademarks*